(12) United States Patent
Kreider et al.

(10) Patent No.: US 9,879,102 B2
(45) Date of Patent: Jan. 30, 2018

(54) MIXED DECYL MERCAPTANS COMPOSITIONS AND USE THEREOF AS CHAIN TRANSFER AGENTS

(71) Applicant: Chevron Phillips Chemical Company LP, The Woodlands, TX (US)

(72) Inventors: Jason L. Kreider, Copan, OK (US); Michael S. Matson, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/463,867

(22) Filed: Mar. 20, 2017

(65) Prior Publication Data
US 2017/0190811 A1 Jul. 6, 2017

Related U.S. Application Data

(60) Continuation of application No. 15/284,802, filed on Oct. 4, 2016, now Pat. No. 9,631,039, which is a division of application No. 14/981,428, filed on Dec. 28, 2015, now Pat. No. 9,512,248.

(51) Int. Cl.
C08F 12/08 (2006.01)
C08F 112/08 (2006.01)
C07C 321/04 (2006.01)

(52) U.S. Cl.
CPC .......... *C08F 112/08* (2013.01); *C07C 321/04* (2013.01)

(58) Field of Classification Search
CPC .............................. C08F 12/08; C07C 321/04
See application file for complete search history.

(56) References Cited

U.S. PATENT DOCUMENTS

| | | | |
|---|---|---|---|
| 1,774,183 | A | 8/1930 | Moses et al. |
| 2,125,337 | A | 8/1938 | Gaudin |
| 2,411,961 | A | 12/1946 | Evans et al. |
| 2,551,813 | A | 5/1951 | Pinkney et al. |
| 3,059,774 | A | 10/1962 | Wilson |
| 3,219,709 | A | 11/1965 | Louthan |
| 3,221,056 | A | 11/1965 | Louthan |
| 3,419,614 | A | 12/1968 | Doss |
| 4,119,549 | A | 10/1978 | Davis |
| 4,211,644 | A | 7/1980 | Wiechers |
| 4,274,950 | A | 6/1981 | Larribau |
| 4,439,314 | A * | 3/1984 | Parlman .................. B03D 1/008 209/166 |
| 4,594,151 | A | 6/1986 | Delourme et al. |
| 4,822,483 | A | 4/1989 | Klimpel et al. |
| 5,183,856 | A | 2/1993 | Kitagawa et al. |
| 5,304,683 | A | 4/1994 | Sattich |
| 5,310,683 | A * | 5/1994 | Godec .................. G01N 21/766 422/52 |
| 6,242,489 | B1 | 6/2001 | Pinney |
| 6,288,006 | B1 * | 9/2001 | Arretz ...................... B01J 37/20 502/216 |
| 6,417,306 | B1 | 7/2002 | Ueda et al. |
| 6,827,220 | B1 | 12/2004 | Young et al. |
| 6,844,290 | B1 * | 1/2005 | Maas ...................... B01J 31/143 502/103 |
| 7,014,048 | B2 | 3/2006 | Anglerot et al. |
| 7,105,602 | B1 | 9/2006 | Sunagawa et al. |
| 7,217,843 | B2 | 5/2007 | Hasenberg et al. |
| 7,461,745 | B2 | 12/2008 | Young et al. |
| 7,989,655 | B2 | 8/2011 | Refvik et al. |
| 8,592,550 | B2 | 11/2013 | Frijns et al. |
| 8,883,907 | B2 | 11/2014 | Moraru et al. |
| 9,505,011 | B1 | 11/2016 | Byers et al. |
| 9,512,071 | B1 | 12/2016 | Matson et al. |
| 9,512,248 | B1 | 12/2016 | Kreider et al. |
| 9,527,090 | B1 | 12/2016 | Byers et al. |
| 9,631,039 | B1 | 4/2017 | Kreider et al. |
| 2005/0187391 | A1 | 8/2005 | Knudsen et al. |
| 2006/0173218 | A1 * | 8/2006 | Muller .................. C07C 319/04 568/61 |

(Continued)

FOREIGN PATENT DOCUMENTS

CN 105985774 A 10/2016
EP 2397503 A1 12/2011

(Continued)

OTHER PUBLICATIONS

Filing receipt and specification for patent application entitled "Mixed Decyl Mercaptans Compositions and Methods of Making Same," by Jason L. Kreider, filed on Aug. 4, 2017 as U.S. Appl. No. 15/669,097, 122 pages.
Filing receipt and specification for patent application entitled "Mixed Decyl Mercaptans Compositions and Methods of Making Same," by Michael S. Matson, et al., filed on Jun. 26, 2017 as U.S. Appl. No. 15/632,910, 101 page.
Office Action dated Aug. 2, 2017 (22 pages), U.S. Appl. No. 15/632,910, filed Jun. 26, 2017.
Technical Data Sheet entitled NEODENE® 14/16 Higher Olefins, Nov. 2015, 2 pages, Shell Chemicals.
Technical Data Sheet entitled NEODENE® 134 IO Higher Olefins, Nov. 2015, 2 pages, Shell Chemicals.
Technical Data Sheet entitled NEODENE® 1112 IO Higher Olefins, Nov. 2015, 2 pages, Shell Chemicals.
Filing receipt and specification for patent application entitled "Mixed Decyl Mercaptans Compositions and Methods of Making Same," by Michael S. Matson, et al., filed on Oct. 18, 2016 as U.S. Appl. No. 15/296,837.
Foreign communication from a related counterpart application—International Search Report and Written Opinion, PCT/US2015/040433, dated Feb. 23, 2016, 14 pages.

(Continued)

*Primary Examiner* — Robert Harlan
(74) *Attorney, Agent, or Firm* — Conley Rose, P.C.; Rodney B. Carroll; Chad E. Walter

(57) ABSTRACT

A chain transfer agent composition comprises at least one branched $C_{10}$ mercaptan selected from 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, or combinations thereof. The chain transfer agent composition can be a component of an emulsion polymerization mixture and can be used in a process for emulsion polymerization for the production of polymers, for example, via free-radical polymerization.

11 Claims, 10 Drawing Sheets

(56) References Cited

U.S. PATENT DOCUMENTS

| | | |
|---|---|---|
| 2007/0244248 A1 | 10/2007 | Behles |
| 2009/0264669 A1 | 10/2009 | Upshaw |
| 2010/0274065 A1 | 10/2010 | Sydora |
| 2011/0269930 A1 | 11/2011 | Edel et al. |
| 2014/0221692 A1 | 8/2014 | Netemeyer et al. |

FOREIGN PATENT DOCUMENTS

| | | | |
|---|---|---|---|
| WO | 8606983 | A1 | 12/1986 |
| WO | 0147839 | A1 | 7/2001 |
| WO | 2014094114 | A1 | 6/2014 |
| WO | 2017010998 | A1 | 1/2017 |

OTHER PUBLICATIONS

"Group notation revised in periodic table," Feb. 4, 1985, pp. 26-27, C&EN.
McNaught, Alan D., et al., "Compendium of Chemical Terminology," IUPAC Recommendations, Second edition, 1997, 5 pages, Wiley-Blackwell.
Office Action dated Dec. 16, 2016 (24 pages), U.S. Appl. No. 15/296,837, filed Oct. 18, 2016.
Duffey, H. R., et al., "Effect of Catalysts on the Reaction between Olefins and Hydrogen Sulfide," Industrial and Engineering chemistry, Jan. 1934, pp. 91-93, vol. 26, No. 1.
Foreign communication from a related counterpart application—International Search Report and Written Opinion, PCT/US2016/058822, dated Jan. 16, 2017, 8 pages.
Foreign communication from a related counterpart application—International Search Report and Written Opinion, PCT/US2016/058818, dated Jan. 23, 2017, 14 pages.
Matsumoto, Y., et al,. "Mfr of polyurethane of resin for waterproof fabric—by radical polymerisation of polyoxyethylene mono:alkyl:ether (meth)acrylate with mercaptan-based chain transfter agent, poly:ol, and organic poly:isocyanate," WPI, 1992, 2 pages, XP-002755753, Thomson.
Sorokina, L. I., et al., "Chain transfer reactions by aliphatic mercaptans in the high-tempurature polymerization of methlmethacrylate," Polymer Science U.S.S.R., Jan. 1, 1983, pp. 2414-2418, vol. 25, No. 10, Pergamon Press Ltd.
Vaughan, W. E., et al., "The Photo-Additions of Hydrogen Sulfide to Olefinic Bonds," The Journal of Organic Chemistry, Nov. 1942, pp. 472-476, vol. 7, No. 6.
Van Zijll Langhout, W. C., et al., "The addition of hydrogen sulphide to alkenes," Journal of Applied Chemistry, Jun. 4, 1954, pp. 285-288, vol. 4, No. 6, Journal of Applied Chemistry.
Notice of Allowance dated Mar. 28, 2017 (16 pages), U.S. Appl. No. 15/296,837, filed Oct. 18, 2016.
Final Office Action dated Nov. 21, 2017 (11 pages), U.S. Appl. No. 15/632,910, filed Jun. 26, 2017.

\* cited by examiner

MIXED DECYL MERCAPTANS COMPOSITIONS AND USE THEREOF AS CHAIN TRANSFER AGENTS

CROSS-REFERENCE TO RELATED APPLICATIONS

This application is a continuation of and claims priority to U.S. patent application Ser. No. 15/284,802 filed Oct. 4, 2016 and entitled "Mixed Decyl Mercaptans Compositions and Use Thereof as Chain Transfer Agents," which is a divisional of and claims priority to U.S. patent application Ser. No. 14/981,428 filed Dec. 28, 2015 and entitled "Mixed Decyl Mercaptans Compositions and Use Thereof as Chain Transfer Agents," which are incorporated by reference herein in their entirety.

TECHNICAL FIELD

The present disclosure relates to compositions containing mixed decyl mercaptans and/or mixed decyl sulfides and use thereof as chain transfer agents. More specifically, the present disclosure relates to chain transfer agent compositions containing branched decyl mercaptans.

BACKGROUND

Mercaptans, which are also known as thiols, are organic compounds used in diverse applications. Some mercaptans can be used as precursors for agriculture chemicals or as natural gas additives. While processes for making mercaptans are available, preparing individual mercaptans can be costly due to numerous purification steps required for the feedstock and/or mercaptan product. However, many applications may not require a single pure mercaptan compound, but could utilize mercaptan mixtures. Thus, there is a need to develop mercaptan compositions suitable for such applications, and methods of making same.

One such application is emulsion polymerization. In the past, mercaptans such as n-dodecyl mercaptans (NDDM) and tert-dodecyl mercaptans (TDDM) have been used as chain transfer agents in emulsion polymerization. However, use of these and other mercaptans are sometimes avoided because they can be undesirably odorous. Thus, there is an ongoing need for mercaptans which are more desirable for use as chain transfer agents in emulsion polymerization.

BRIEF SUMMARY

Disclosed herein is a chain transfer agent composition comprising at least one branched $C_{10}$ mercaptan selected from 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, or combinations thereof.

Also disclosed herein is an emulsion polymerization reaction mixture comprising a chain transfer agent composition, optionally one or more monomer, optionally one or more surfactant, optionally one or more polymerization initiator, and optionally water. The chain transfer agent composition in the mixture can comprise at least one branched $C_{10}$ mercaptan selected from 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, or combinations thereof.

Also disclosed herein is a process for emulsion polymerization comprising introducing into an emulsion polymerization mixture a chain transfer agent composition. The chain transfer agent composition comprises at least one branched $C_{10}$ mercaptan selected from 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, or combinations thereof.

BRIEF DESCRIPTION OF THE DRAWINGS

For a detailed description of the preferred embodiments of the disclosed compositions and methods of making same, reference will now be made to the accompanying drawings in which.

DETAILED DESCRIPTION

Figure 1:
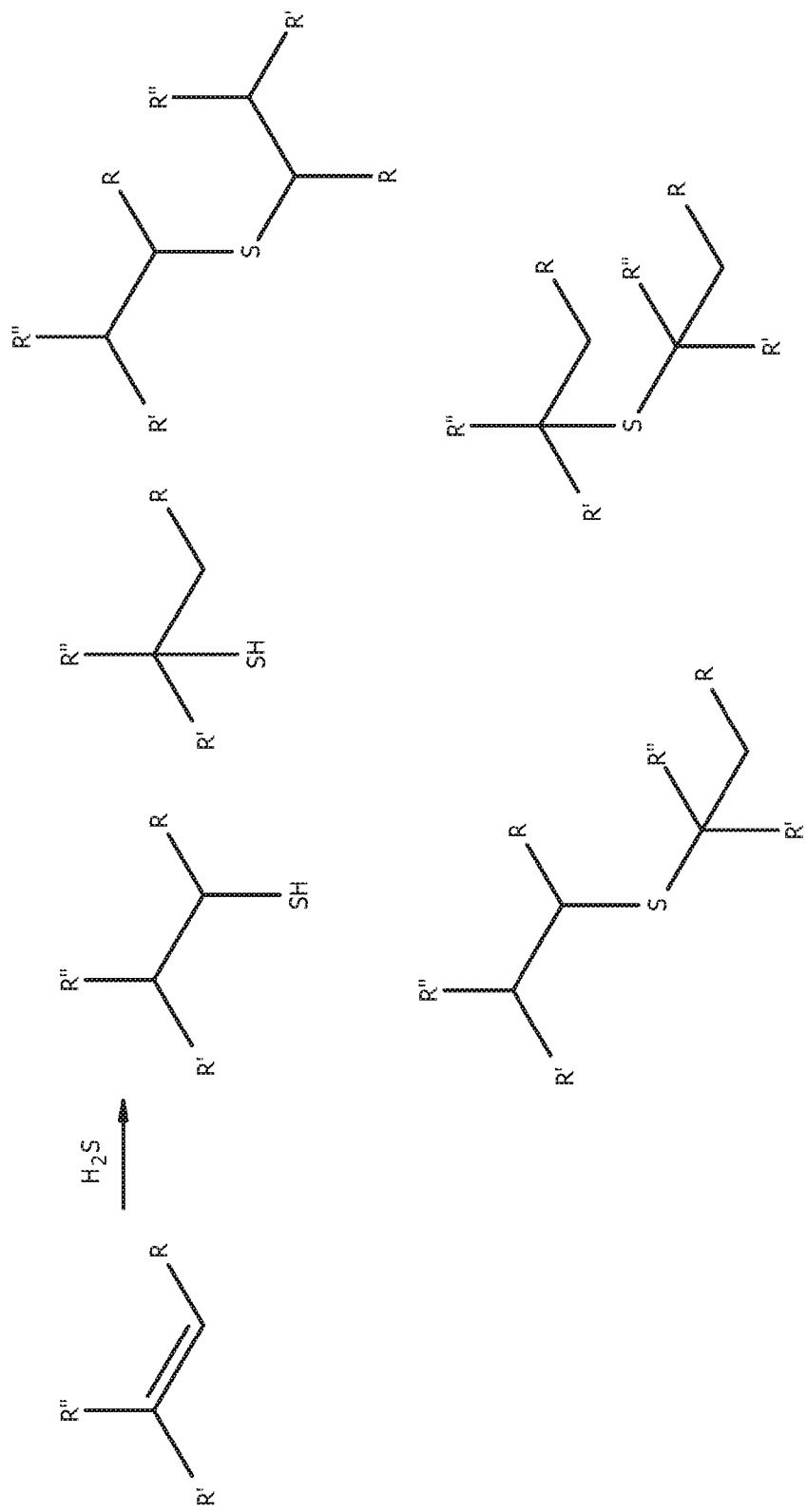
FIG. 1 displays a reaction schematic for addition of hydrogen sulfide ($H_2S$) to an olefin.

To define more clearly the terms used herein, the following definitions are provided. Unless otherwise indicated, the following definitions are applicable to this disclosure. If a term is used in this disclosure, but is not specifically defined herein, the definition from the IUPAC Compendium of Chemical Terminology, 2$^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News*, 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. The term "consisting essentially of" occupies a middle ground between closed terms like "consisting of" and fully open terms like "comprising." Absent an indication to the contrary, when describing a compound or composition, "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which is utilized and it is possible to have different transitional terms or phrases utilized with different features within a claim. For example, a method can comprise several recited steps (and other non-recited steps), but utilize a catalyst system preparation consisting of specific steps, or alternatively, consisting essentially of specific steps, but utilize a catalyst system comprising recited components and other non-recited components.

While compositions and methods are described in terms of "comprising" (or other broad term) various components and/or steps, the compositions and methods can also be described using narrower terms, such as "consist essentially of" or "consist of" the various components and/or steps.

The terms "a," "an," and "the" are intended, unless specifically indicated otherwise, to include plural alternatives, e.g., at least one.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers, unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers, whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" can formally be derived by removing one hydrogen atom from an alkane, while an "alkylene group" can formally be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," and which encompasses an "alkyl group," an "alkylene group," and materials having three or more hydrogens atoms, as necessary for the situation, removed from the alkane. Throughout, the disclosure of a substituent, ligand, or other chemical moiety that can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, and tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from a carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms, such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc., such multiple bonds can be identified by use of the term "mono," "di," "tri," etc., within the name. For example, alkamonoenes, alkadienes, and alkatrienes refer to linear or branched acyclic hydrocarbon olefins having only one carbon-carbon double bond (acyclic having a general formula of $C_nH_{2n}$), only two carbon-carbon double bonds (acyclic having a general formula of $C_nH_{2n-2}$), and only three carbon-carbon double bonds (acyclic having a general formula of $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2 position (a vinylidene) and/or the 3 position or higher with respect to the olefin double bond. The term "vinylidene" whenever used in this specification and claims refers to an alpha olefin having a branch at the 2 position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic monoolefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms.

The terms "lights," "light fraction," or "light compounds" whenever used in this specification and claims refers to compounds present in the reaction product with equal to or less than about 9 carbon atoms ($C_9$) per molecule. Nonlimiting examples of $C_{9-}$ compounds that can be in the reaction product include $C_{9-}$ monoolefins (e.g., unreacted $C_{9-}$ monoolefins), $C_{9-}$ mercaptans, $C_{9-}$ alkanes, $C_{9-}$ alcohols, cyclohexane, methylcyclopentane, methylcyclohexane, benzene, toluene, ethylbenzene, xylene, mesitylene, 2-ethyl-1-hexanol, and the like, or combinations thereof. Unless otherwise specifically indicated herein, the terms "lights," "light fraction," or "light compounds" whenever used in this specification and claims excludes hydrogen sulfide, as $H_2S$ is typically substantially consumed during the preceding reaction and/or removed from the reaction product (as discussed in more detail herein) prior to further processing of the reaction product (e.g., distillation thereof). For example, $H_2S$ can be removed from the reaction product via distillation, stripping, flashing, or other suitable means known to those of skill in the art without removing any substantial amounts of the "lights," "light fraction," or "light compounds" from the reaction product. Not wanting to be limited by theory, this definition of "lights," "light fraction," or "light compounds" includes any compounds with about nine or less carbon atoms present in the reaction product that can be detected, even in trace amounts. As is known to one of skill in the art, the light fraction can also contain trace amounts of lower carbon number sulfides.

The terms "intermediates" or "intermediate fraction" whenever used in this specification and claims typically refers to compounds with about ten to seventeen carbon atoms ($C_{10-17}$) per molecule. Nonlimiting examples of $C_{10-17}$ compounds include $C_{10}$ mercaptans (including both branched and non-branched $C_{10}$ mercaptans), $C_{12-17}$ mercaptan isomers, $C_{12}$-$C_{17}$ sulfides, and the like, or combinations thereof. Not wanting to be limited by theory, this definition of "intermediates" or "intermediate fraction" includes any compounds with about ten to seventeen carbon atoms present in the reaction product that can be detected, even in trace amounts. As is known to one skilled in the art, the intermediate fraction can also contain trace amounts of lower carbon number compounds, including sulfides. In some embodiments, a product can be recovered from the intermediate fraction (e.g., a $C_{10}$ mercaptan fraction), and the remaining $C_{11}$ to $C_{17}$ compounds (e.g., $C_{12-16}$ mercaptans) can be referred to as the intermediate fraction.

The terms "heavies" or "heavy fraction" whenever used in this specification and claims refers to compounds with about eighteen or more carbon atoms ($C_{18+}$) per molecule. Nonlimiting examples of $C_{18+}$ products include $C_{18}$ sulfides, $C_{20}$ sulfides, $C_{24}$ sulfides, $C_{28}$ sulfides, $C_{32}$ sulfides, $C_{18}$ mercaptans, and the like, or combinations thereof. As is known to those of skill in the art, the heavy fraction can also contain trace amounts of lower carbon number compounds, including mercaptans and sulfides.

These light, intermediate, and heavy fractions can be referred to as "rough-cuts," in that they contain a plurality of compounds spread across a range of carbon atoms, i.e., a plurality of compounds having a different number of carbon atoms (e.g., a rough cut comprising $C_{10}$, $C_{11}$, $C_{12}$, $C_{13}$, $C_{14}$, $C_{15}$, $C_{16}$, $C_{17}$, etc. compounds). These rough cuts are in contrast to one or more "fine-cuts" that contain a fewer number of compounds than the rough-cuts, for example, a $C_{10}$ fine cut (e.g., a $C_{10}$ mercaptan fraction) derived from or otherwise recovered separately from the rough cut. Accordingly, a rough cut can be comprised of a number of fine cuts, for example where a plurality of cuts are taken via distillation over a period of time and across a ramped temperature range, and referred to collectively as a rough cut or individually as fine cuts. Those of ordinary skill in the art can produce a fine-cut fraction from a rough-cut fraction, for example via further distillation (e.g., a $C_{10}$ splitter, a $C_{20}$ splitter, etc.) or other purification technique.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as a minimum value can be alternatively stated as "at least" or "greater than or equal to" any recited minimum value for the feature disclosed herein. Features within this disclosure that are provided as a maximum value can be alternatively stated as "less than or equal to" or "below" any recited maximum value for the feature disclosed herein.

Within this disclosure, the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a phenyl group having a non-hydrogen substituent group at the 4 position and hydrogen or any non-hydrogen group at the 2, 3, 5, and 6 positions.

Use of the term "optionally" with respect to any element of a claim is intended to mean that the subject element is required, or alternatively, is not required. Both alternatives are intended to be within the scope of the claim.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms. Moreover, other identifiers or qualifying terms can be utilized to indicate the presence or absence of a particular substituent, a particular regiochemistry and/or stereochemistry, or the presence or absence of a branched underlying structure or backbone.

Processes and/or methods described herein utilize steps, features, and compounds which are independently described herein. The process and methods described herein may or may not utilize step identifiers (e.g., 1), 2), etc., a), b), etc., or i), ii), etc.), features (e.g., 1), 2), etc., a), b), etc., or i), ii), etc.), and/or compound identifiers (e.g., first, second, etc.). However, it should be noted that processes and/or methods described herein can have multiple steps, features (e.g., reagent ratios, formation conditions, among other considerations), and/or multiple compounds having the same general descriptor. Consequently, it should be noted that the processes and/or methods described herein can be modified to use an appropriate step or feature identifier (e.g., 1), 2), etc., a), b), etc., or i), ii), etc.) and/or compound identifier (e.g., first, second, etc.) regardless of step, feature, and/or compound identifier utilized in a particular aspect and/or embodiment described herein and that step or feature identifiers can be added and/or modified to indicate individual different steps/features/compounds utilized within the process and/or methods without detracting from the general disclosure.

Embodiments disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

The weight percent compositional aspects of the various compositions described herein (e.g., the weight percent of one or more compounds present in a composition) can be determined by gas chromatography (GC), gas chromatography-mass spectroscopy (GC-MS), Raman spectroscopy, nuclear magnetic resonance (NMR) spectroscopy, or any other suitable analytical method known to those of skill in the art. For example, unless otherwise indicated, the weight percent compositional aspects of the various compositions described herein (e.g., the weight percent of the various sulfur-containing compounds such as $C_{10}$ mercaptans and $C_{20}$ sulfides present in the compositions such as the crude, light fraction, intermediate fraction, heavy faction, etc.) can be determined using a gas chromatograph with a flame ionization detector (GC-FID) detector based on the total GC peak areas (as described herein) and reported as gas chromatography (GC) area percent (GC area %), which is a common analytical technique for compositions comprising sulfur-containing compounds. While not wishing to be bound by this theory, it is believed that the amount in area % is very similar to the amount in weight percent (wt. %), and these respective amounts need not be exactly equivalent or interchangeable in order to be understood by a person of ordinary skill.

In an embodiment, a process of the present disclosure comprises reacting, in a reactor, hydrogen sulfide ($H_2S$) and a feedstock comprising one or more branched $C_{10}$ monoolefins in the presence of an initiating agent to produce a crude composition (also referred to as a crude product); wherein the branched $C_{10}$ monoolefins comprise 5-methyl-1-nonene, 3-propyl-1-heptene, 4-ethyl-1-octene, 2-butyl-1-hexene, or combinations thereof; and wherein the crude composition comprises branched $C_{10}$ mercaptans and branched $C_{20}$ sulfides.

The crude composition can be further processed, for example via distillation, to yield one or more products (also referred to as distilled, purified, refined, finished, or final products) selected from the group consisting of mercaptan compositions (e.g., a composition comprising one or more branched $C_{10}$ mercaptans), sulfide compositions (e.g., a composition comprising one or more branched $C_{20}$ sulfides); and compositions having both mercaptans (e.g., branched $C_{10}$ mercaptans) and sulfides (e.g., branched $C_{20}$ sulfides), referred to as mercaptan/sulfide compositions.

In an embodiment, a mercaptan composition comprises branched $C_{10}$ mercaptans selected from the group consisting of 5-methyl-1-mercapto-nonane, 3-propyl-1-mercapto-heptane, 4-ethyl-1-mere apto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof.

In an embodiment, a sulfide composition comprises branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

In an embodiment, a mercaptan/sulfide composition comprises (A) branched $C_{10}$ mercaptans selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof; and (B) branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

The mercaptan compositions, sulfide compositions, and mercaptan/sulfide compositions can be salable or otherwise used for a variety of end uses such as mining ore collector compositions and chain transfer agents.

In an embodiment, the compositions disclosed herein can be prepared by a process comprising reacting, in a reactor, hydrogen sulfide ($H_2S$) and a feedstock comprising one or more branched $C_{10}$ monoolefins in the presence of an initiating agent to produce a crude (reaction product) composition, wherein the branched $C_{10}$ monoolefins comprise 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

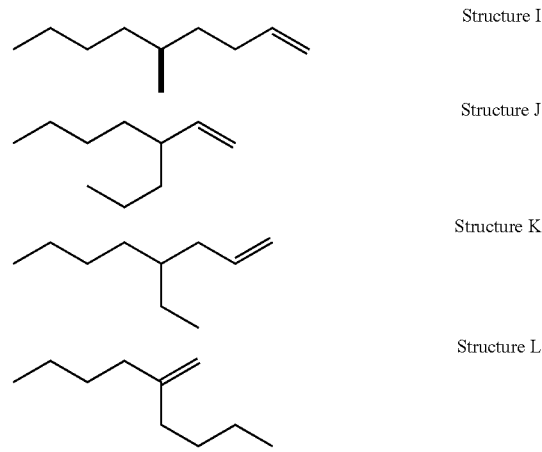

Structure I

Structure J

Structure K

Structure L

Any feedstock comprising one or more branched $C_{10}$ monoolefins of the type described herein can be used, for example a feedstock obtained from a commercial petroleum refining or petrochemical process. Such feedstocks can comprise other olefins in addition to the one or more branched $C_{10}$ monoolefins of the type described herein, for example linear $C_{10}$ monoolefins as well as olefins having more or less than 10 carbon atoms. In an embodiment, the feedstock comprises one or more branched $C_{10}$ monoolefins and is obtained from a 1-hexene production process effluent stream. In various embodiments, a feedstock obtained from a 1-hexene production process effluent stream can comprise $C_{10}$ monoolefins (e.g., branched and/or linear $C_{10}$ monoolefins) as well as olefins having more or less than 10 carbon atoms.

In an embodiment, the feedstock can comprise (a) at least about 76 mol %, alternatively at least about 78 mol %, alternatively at least about 80 mol %, or alternatively at least about 82 mol % $C_{10}$ monoolefins, and (b) at least about 1 mol %, alternatively at least about 2 mol %, alternatively at least about 3 mol %, or alternatively at least about 4 mol % $C_{14}$ monoolefins. In an embodiment, the feedstock can comprise (a) from about 76 mol % to about 92 mol %, alternatively from about 78 mol % to about 90 mol %, alternatively from about 80 mol % to about 88 mol %, or alternatively from about 82 mol % to about 86 mol % $C_{10}$ monoolefins; and (b) from about 1 mol % to about 12 mol %, alternatively from about 2 mol % to about 10 mol %, alternatively from about 3 mol % to about 8 mol %, or alternatively from about 4 mol % to about 7 mol % $C_{14}$ monoolefins. For purposes of the disclosure herein, a feedstock comprising (a) at least about 76 mol % $C_{10}$ monoolefins, and (b) at least about 1 mol % $C_{14}$ monoolefins can also be referred to as a "first feedstock." In an embodiment, the first feedstock is obtained from a 1-hexene production process effluent stream, for example an effluent stream obtained from a 1-hexene production process of the type disclosed in co-pending International Patent Application PCT/US2015/40433, which is incorporated by reference herein in its entirety.

In another embodiment, the feedstock can comprise at least about 95 mol %, alternatively at least about 96 mol %, alternatively at least about 97 mol %, alternatively at least about 98 mol %, or alternatively at least about 99 mol % $C_{10}$ monoolefins. For purposes of the disclosure herein, a feedstock comprising at least about 95 mol % $C_{10}$ monoolefins can also be referred to as a "second feedstock." In an embodiment, the second feedstock can be produced by purifying the first feedstock, such as for example by distillation of an effluent stream obtained from a 1-hexene production process of the type disclosed in co-pending International Patent Application PCT/US2015/40433, which is incorporated by reference herein in its entirety.

In an embodiment, the $C_{10}$ monoolefins of any feedstock described herein (e.g., a first feedstock or a second feedstock) can comprise, can consist essentially of, or can be, 2-butyl-1-hexene, 3-propyl-1-heptene, 4-ethyl-1-octene, and 5-methyl-1-nonene. In an embodiment, the $C_{10}$ monoolefins of any feedstock described herein can comprise i) at least about 3 mol %, alternatively at least about 4 mol %, alternatively at least about 5 mol %, alternatively at least about 6 mol %, alternatively at least about 7 mol %, or alternatively at least about 8 mol % 2-butyl-1-hexene (represented by Structure L), ii) at least about 8 mol %, alternatively at least about 9 mol %, alternatively at least about 10 mol %, alternatively at least about 11 mol %, alternatively at least about 12 mol %, or alternatively at least about 13 mol % 3-propyl-1-heptene (represented by Structure J), iii) at least about 6 mol %, alternatively at least about 7 mol %, alternatively at least about 8 mol %, alternatively at least about 9 mol %, alternatively at least about 10 mol %, or alternatively at least about 11 mol % 4-ethyl-1-octene (represented by Structure K), and iv) at least about 20 mol %, alternatively at least about 22 mol %, alternatively at least about 24 mol %, alternatively at least about 26 mol %, alternatively at least about 28 mol %, or alternatively at least about 30 mol % 5-methyl-1-nonene (represented by Structure I).

In an embodiment, the $C_{10}$ monoolefins of any feedstock described herein (e.g., a first feedstock or a second feedstock) can have a molar ratio of 2-butyl-1-hexene to 5-methyl-1-nonene of at least about 2:1, alternatively at least about 2.4:1, alternatively at least about 2.6:1, or alternatively at least about 2.8:1. In an embodiment, the $C_{10}$ monoolefins of any feedstock described herein can have a molar ratio of 3-propyl-1-heptene to 5-methyl-1-nonene of at least about 1.2:1, alternatively at least about 1.4:1, alternatively at least about 1.6:1, or alternatively at least about 1.8:1. In an embodiment, the $C_{10}$ monoolefins of any feedstock described herein can have a molar ratio of 4-ethyl-1-octene to 5-methyl-1-nonene of at least about 1.6:1, alternatively at least about 1.7:1, alternatively at least about 1.9:1, or alternatively at least about 2.1:1. In an embodiment, the $C_{10}$ monoolefins of any feedstock described herein can have a molar ratio of 2-butyl-1-hexene to 5-methyl-1-nonene of at least about 2:1, alternatively at least about 2.4:1, alternatively at least about 2.6:1, or alternatively at least about 2.8:1; a molar ratio of 3-propyl-1-heptene to 5-methyl-1-nonene of at least about 1.2:1, alternatively at least about 1.4:1, alternatively at least about 1.6:1, or alternatively at least about 1.8:1; and a molar ratio of 4-ethyl-1-octene to 5-methyl-1-nonene of at least about 1.6:1, alternatively at least about 1.7:1, alternatively at least about 1.9:1, or alternatively at least about 2.1:1.

In an embodiment, the $C_{10}$ monoolefins of any feedstock described herein (e.g., a first feedstock or a second feedstock) can comprise linear $C_{10}$ monoolefins. In such embodiment, the linear $C_{10}$ monoolefins can comprise, can consist essentially of, or can be, 1-decene, 4-decene, 5-decene, or combinations thereof; alternatively, 1-decene; alternatively, 4-decene and/or 5-decene; alternatively, 4-decene; or alternatively, 5-decene. In an embodiment, the $C_{10}$ monoolefins of any feedstock described herein can comprise less than or equal to about 26 mol %, alternatively less than or equal to about 24 mol %, alternatively less than or equal to about 22 mol %, alternatively less than or equal to about 20 mol %, or alternatively less than or equal to about 18 mol % linear $C_{10}$ monoolefins. In an embodiment, the $C_{10}$ monoolefins of any feedstock described herein can comprise from about 1 mol % to about 16 mol %, alternatively from about 2 mol % to about 15 mol %, alternatively from about 3 mol % to about 14 mol %, alternatively from about 4 mol % to about 13 mol %, or alternatively from about 6 mol % to about 12 mol % 4-decene and/or 5-decene. In some embodiments, the $C_{10}$ monoolefins of any feedstock described herein can comprise less than or equal to about 10 mol %, alternatively less than or equal to about 9 mol %, alternatively less than or equal to about 8 mol %, alternatively less than or equal to about 7 mol %, or alternatively less than or equal to about 6 mol % 1-decene. In other embodiments, the $C_{10}$ monoolefins of any feedstock described herein can comprise from about 0.5 mol % to about 9 mol %, alternatively from about 1 mol % to about 8 mol %, alternatively from about 1.5 mol % to about 7 mol %, or alternatively from about 2 mol % to about 6 mol % 1-decene.

In an embodiment, the first feedstock disclosed herein can further comprise $C_{9-}$ monoolefins, $C_{11+}$ monoolefins, or combinations thereof; alternatively, $C_{9-}$ monoolefins; or alternatively, $C_{11+}$ monoolefins. In an embodiment, the $C_{9-}$ monoolefins can comprise, can consist essentially of, or can be, a $C_7$ monoolefin, a $C_8$ monoolefin, a $C_9$ monoolefin, or combinations thereof; alternatively, a $C_7$ monoolefin; alternatively, a $C_8$ monoolefin; or alternatively, a $C_9$ monoolefin. In some embodiments, the $C_{9-}$ monoolefins can comprise, can consist essentially of, or can be, a $C_8$ monoolefin. In an embodiment, the $C_{11+}$ monoolefins can comprise, can consist essentially of, or can be, a $C_{11}$ monoolefin, a $C_{12}$ monoolefin, a $C_{13}$ monoolefin, a $C_{14}$ monoolefin, a $C_{15}$ monoolefin, a $C_{16}$ monoolefin, a $C_{17}$ monoolefin, a $C_{18}$ monoolefin, or combinations thereof; alternatively, a $C_{11}$ monoolefin; alternatively, a $C_{12}$ monoolefin; alternatively, a $C_{13}$ monoolefin; alternatively, a $C_{14}$ monoolefin; alternatively, a $C_{15}$ monoolefin; alternatively, a $C_{16}$ monoolefin; alternatively, a $C_{17}$ monoolefin; or alternatively, a $C_{18}$ monoolefin. In some embodiments, the $C_{11+}$ monoolefins can comprise, can consist essentially of, or can be, a $C_{12}$ monoolefin, a $C_{16}$ monoolefin, a $C_{18}$ monoolefin, or combinations thereof; alternatively, a $C_{12}$ monoolefin; alternatively, a $C_{16}$ monoolefin; or alternatively, a $C_{18}$ monoolefin.

In an embodiment, the first feedstock disclosed herein can further comprise $C_8$ monoolefins, $C_{12}$ monoolefins, $C_{16}$ monoolefins, $C_{18}$ monoolefins, or combinations thereof; alternatively, $C_8$ monoolefins; alternatively, $C_{12}$ monoolefins; alternatively, $C_{16}$ monoolefins and/or $C_{18}$ monoolefins;

alternatively, $C_{16}$ monoolefins; or alternatively, $C_{18}$ monoolefins. In an embodiment, the $C_8$ monoolefins can comprise 1-octene. In an embodiment, the $C_{12}$ monoolefins can comprise 1-dodecene.

In an embodiment, the first feedstock can further comprise from about 0.1 mol % to about 5 mol %, alternatively from about 0.25 mol % to about 4 mol %, or alternatively from about 0.5 mol % to about 3 mol % $C_{12}$ monoolefins. In such embodiment, the $C_{12}$ monoolefins can comprise from about 54 mol % to about 74 mol %, alternatively from about 56 mol % to about 72 mol %, alternatively from about 58 mol % to about 70 mol %, or alternatively from about 60 mol % to about 68 mol % 1-dodecene.

In an embodiment, the first feedstock can further comprise from about 0.1 mol % to about 5 mol %, alternatively from about 0.25 mol % to about 4 mol %, or alternatively from about 0.5 mol % to about 3 mol % $C_8$ monoolefins. In such embodiment, the $C_8$ monoolefins can comprise at least about 95 mol %, alternatively at least about 96 mol %, alternatively at least about 97 mol %, alternatively at least about 98 mol %, or alternatively at least about 99 mol % 1-octene.

In an embodiment, the first feedstock can further comprise from about 0.05 mol % to about 2 mol %, alternatively from about 0.04 mol % to about 1.5 mol %, alternatively from about 0.06 mol % to about 1.25 mol %, alternatively from about 0.08 mol % to about 1 mol %, or alternatively from about 0.1 mol % to about 0.75 mol % $C_{16}$ monoolefins and/or $C_{18}$ monoolefins.

In an embodiment, a feedstock comprising branched $C_{10}$ monoolefins produced in a 1-hexene process can be purified to produce a second feedstock of the type described herein, for example to improve olefin reactivity and resultant mercaptan and/or sulfide purity. A light fraction, comprising $C_{9-}$, can be removed from the feedstock and any $C_{10}$ olefin isomers can be collected overhead to obtain a high purity (>95%) $C_{10}$ monoolefin fraction as the second feedstock. This high purity $C_{10}$ monoolefin fraction (i.e., second feedstock) comprises little or no non-olefin impurities or $C_{ii}$ to $C_{17}$ compounds. The high purity $C_{10}$ olefin can be reacted with $H_2S$ to produce a crude composition. Reaction conditions to produce a crude composition from the high purity $C_{10}$ monoolefin fraction (i.e., a second feedstock) can be identical to the reaction conditions disclosed for the feedstock comprising branched $C_{10}$ monoolefins produced in a 1-hexene process used as received without further purification (i.e., a first feedstock). The major difference between reacting a first feedstock and a second feedstock is the composition of the crude composition and any resulting purified or partially purified products (e.g., fractions or cuts taken from the crude composition). For the second feedstock (e.g., a high purity (>95%) $C_{10}$ monoolefin fraction), the crude composition can comprise residual $H_2S$, unreacted $C_{10}$ olefin, $C_{10}$ mercaptan isomers, and $C_{10}H_{21}$—S—$C_{10}H_{21}$ sulfides and minimal other mercaptans or sulfides. After removal of $H_2S$ and $C_{9-}$ lights from the crude composition, the resultant partially purified product will contain $C_{10}$ mercaptan isomers and $C_{20}$ sulfides, but will not contain any of the intermediate mercaptans and asymmetric sulfide components formed by reactions of olefins having less than or greater than 10 carbon atoms (because there were minimal, if any, such olefins having less than or greater than 10 carbon atoms in the purified feedstock). While not wishing to be bound by theory, it is believed that the intermediate mercaptans and asymmetric sulfide components can be produced from the reaction of $C_{10}$ mercaptans with other non-$C_{10}$ olefins.

In an embodiment, $H_2S$ and a feedstock comprising one or more branched $C_{10}$ monoolefins can be reacted at an $H_2S$ to olefin molar ratio of from about 1:1 to about 20:1, alternatively from about 2:1 to about 15:1, or alternatively from about 3:1 to about 10:1.

In an embodiment, $H_2S$ and a feedstock comprising one or more branched $C_{10}$ monoolefins can be reacted at a pressure of from about 30 psig (206 kPag) to about 1,500 psig (10,300 kPag), alternatively from about 100 psig (690 kPag) to about 1,250 psig (8,600 kPag), or alternatively from about 250 psig (1,700 kPag) to about 1,000 psig (6,900 kPag).

In an embodiment, $H_2S$ and a feedstock comprising one or more branched $C_{10}$ monoolefins can be reacted to produce olefin conversion of equal to or greater than about 80%, alternatively equal to or greater than about 85%, or alternatively equal to or greater than about 90%. For purposes of the disclosure herein, an olefin conversion refers to the mol % of olefins that have reacted during the reaction between $H_2S$ and a feedstock in a reactor, with respect to the amount of olefins introduced into the reactor during the same time period.

In an embodiment, the process can comprise reacting $H_2S$ and a feedstock (e.g., a first or second feedstock as described herein) comprising one or more branched $C_{10}$ monoolefins in the presence of an initiating agent to produce a crude composition; wherein the initiating agent comprises ultraviolet (UV) radiation. In such embodiment, the UV radiation can be any UV radiation capable of initiating the reaction of the olefins present in the feedstock and $H_2S$. In some embodiments, the UV radiation can be generated by a medium pressure mercury lamp. As will be appreciated by one of skill in the art, and with the help of this disclosure, although UV radiation can be the initiating agent, other suitable types of light sources can be used.

In an embodiment, $H_2S$ and a feedstock comprising one or more branched $C_{10}$ monoolefins can be reacted in the presence of an initiating agent comprising UV radiation in a batch reactor or a continuous reactor. Nonlimiting examples of continuous reactors suitable for use in the present disclosure include continuous flow reactors, continuous stirred reactors, fixed bed reactors, and the like, or combinations thereof. Nonlimiting examples of batch reactors suitable for use in the present disclosure include UV batch reactors. As will be appreciated by one of skill in the art, and with the help of this disclosure, any other suitable type of batch and continuous reactors can be used for reacting $H_2S$ and a feedstock comprising one or more branched $C_{10}$ monoolefins in the presence of UV radiation. UV reactors and conditions suitable for reacting $H_2S$ and a feedstock comprising one or more branched $C_{10}$ monoolefins in the presence of UV radiation are described in more detail in U.S. Pat. No. 7,989,655, and U.S. Publication No. 20140221692 A1, each of which is incorporated by reference herein in its entirety.

In embodiments where $H_2S$ and a feedstock comprising one or more branched $C_{10}$ monoolefins are reacted in the presence of UV radiation in a continuous reactor, the continuous reactor can be sized and configured to the desired continuous production rate. That is, a person skilled in the art will be able to select an appropriate reaction vessel size, geometry and material (e.g., a transparent material for sidewalls, windows, or internal chambers); along with an appropriate number of UV sources; and arrange the sources and reactor vessel (e.g., place UV sources adjacent a transparent exterior portion of the reaction vessel and/or disposed in transparent chambers within the reactor vessel) to yield a desired continuous production rate.

In embodiments where $H_2S$ and a feedstock comprising one or more branched $C_{10}$ monoolefins are reacted in the presence of UV radiation in a batch reactor, the batch reactor can be characterized by a reaction time of from about 1 minute to about 4 hours, alternatively from about 10 minutes to about 2 hours, or alternatively from about 30 minutes to about 1.5 hours.

In an embodiment, $H_2S$ and a feedstock comprising one or more branched $C_{10}$ monoolefins can be reacted in the presence of UV radiation at a temperature of from about 0° C. to about 100° C., alternatively from about 10° C. to about 70° C., or alternatively from about 15° C. to about 35° C.

In an embodiment, $H_2S$ and a feedstock comprising one or more branched $C_{10}$ monoolefins can be reacted in the presence of UV radiation at a $H_2S$ to olefin molar ratio of from about 1:1 to about 15:1, alternatively from about 2:1 to about 12.5:1, or alternatively from about 5:1 to about 10:1.

In an embodiment, the process can comprise reacting $H_2S$ and a feedstock comprising one or more branched $C_{10}$ monoolefins in the presence of an initiating agent to produce a crude composition; wherein the initiating agent comprises ultraviolet (UV) radiation, and wherein the initiating agent further comprises a phosphite promoter, a photoinitiator, or both.

In an embodiment, the phosphite promoter can be used in an amount of from about 0.01 wt. % to about 5 wt. %, alternatively from about 0.1 wt. % to about 4 wt. %, or alternatively from about 1 wt. % to about 2.5 wt. %, based on a weight of olefins.

In an embodiment, the phosphite promoter can be characterized by formula $P(OR^5)_3$, wherein each $R^5$ can independently be a $C_1$-$C_{18}$ hydrocarbyl group, alternatively $C_1$-$C_{10}$ hydrocarbyl group, alternatively $C_1$-$C_5$ hydrocarbyl group; alternatively a $C_1$-$C_{18}$ alkyl group, alternatively $C_1$-$C_{10}$ alkyl group, alternatively $C_1$-$C_5$ alkyl group; alternatively, a $C_6$-$C_{18}$ aryl group, or alternatively, a $C_6$-$C_{10}$ aryl group. Nonlimiting examples of $R^5$ groups suitable for use in the present disclosure in the phosphite promoter include a methyl group, an ethyl group, a propyl group, a butyl group, a pentyl group, a hexyl group, a heptyl group, an octyl group, a nonyl group, a decyl group; a phenyl group, a tolyl group, a xylyl group, a naphthyl group; and the like, or combinations thereof.

Nonlimiting examples of phosphite promoters suitable for use in the present disclosure include a trialkylphosphite, trimethylphosphite, triethylphosphite, tributylphosphite; a triarylphosphite, triphenylphosphite; and the like, or combinations thereof.

In an embodiment, the photoinitiator can be used in an amount of from about 0.05 wt. % to about 5 wt. %, alternatively from about 0.1 wt. % to about 4 wt. %, or alternatively from about 1 wt. % to about 2.5 wt. %, based on the weight of olefins present in the feed mixture.

Nonlimiting examples of photoinitiators suitable for use in the present disclosure include 1-hydroxy-cyclohexyl-phenyl-ketone, benzophenone, Bis-(2,4,6-trimethylbenzoyl)-phenylphosphineoxide, 2-hydroxy-1-{4-[4-(2-hydroxy-2-methyl-propionyl)-benzyl]-phenyl}-2-methy-1-propan-1-one, 2-hydroxy-2-methyl-1-phenyl-1-propanone, and the like, or combinations thereof.

In an embodiment, the process can comprise reacting $H_2S$ and a feedstock comprising one or more branched $C_{10}$ monoolefins in the presence of UV radiation to produce a crude composition (wherein the crude composition comprises from 50-100 wt. % $C_{10}$ mercaptans, alternatively from 50-90 wt. % $C_{10}$ mercaptans, alternatively from 75-85 wt. % $C_{10}$ mercaptans); wherein the $C_{10}$ mercaptans present in the crude composition further comprise from about 70 wt. % to about 100 wt. %, alternatively from about 70 wt. % to about 95 wt. %, alternatively from about 80 wt. % to about 90 wt. %, or alternatively from about 79 wt. % to about 85 wt. % $C_{10}$ primary mercaptans; from about 0 wt. % to about 30 wt. %, alternatively from about 0 wt. % to about 20 wt. %, alternatively from about 10 wt. % to about 20 wt. %, or alternatively from about 5 wt. % to about 19 wt. % $C_{10}$ secondary mercaptans; and from about 0 wt. % to about 10 wt. %, alternatively from about 0 wt. % to about 5 wt. %, or alternatively from about 0 wt. % to about 3 wt. % $C_{10}$ tertiary mercaptans. For purposes of the disclosure herein, a primary mercaptan is a mercaptan that has the thiol group (—SH) attached to a primary carbon (e.g., a carbon atom that is attached to one and only one other carbon atom). Further, for purposes of the disclosure herein, a secondary mercaptan is a mercaptan that has the thiol group (—SH) attached to a secondary carbon (e.g., a carbon atom that is attached to two and only two other carbon atoms). Further, for purposes of the disclosure herein, a tertiary mercaptan is a mercaptan that has the thiol group (—SH) attached to a tertiary carbon (e.g., a carbon atom that is attached to three and only three other carbon atoms). As will be appreciated by one of skill in the art, and with the help of this disclosure, the make-up of the crude composition, in terms of primary, secondary, and tertiary mercaptans, will depend on the make-up of the feedstock, as well as on the reaction conditions. Further, as will be appreciated by one of skill in the art, and with the help of this disclosure, the make-up of each of the primary, secondary, and tertiary mercaptans will depend on the make-up of the feedstock, as well as on the reaction conditions.

In an embodiment, the $C_{10}$ primary mercaptans can comprise 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 1-mercapto-decane (represented by Structure M), or combinations thereof.

In an embodiment, the $C_{10}$ secondary mercaptans can comprise 4-mercapto-decane (represented by Structure N), 5-mercapto-decane (represented by Structure 0), 5-methyl-2-mercapto-nonane (represented by Structure E), 3-propyl-2-mercapto-heptane (represented by Structure F), 4-ethyl-2-mercapto-octane (represented by Structure G), 2-mercapto-decane (represented by Structure P), or combinations thereof.

In an embodiment, the $C_{10}$ tertiary mercaptans can comprise equal to or greater than about 90 wt. %, alternatively equal to or greater than about 95 wt. %, or alternatively equal to or greater than about 99 wt. % 5-methyl-5-mercapto-nonane (represented by Structure H).

In an embodiment, the process can comprise reacting $H_2S$ and a feedstock (e.g., a first or second feedstock as described herein) comprising one or more branched $C_{10}$ monoolefins in the presence of an initiating agent (e.g., catalyst) to produce a crude composition; wherein the initiating agent comprises an acid catalyst. Nonlimiting examples of acid catalysts suitable for use in the present disclosure include acid washed clays (such as, but not limited to, Filtrol® 24 or Filtrol® 24X); acid washed bentonite; a tetrafluoroethylene polymer resin modified with perfluorovinyl ether groups terminated with sulfonate groups; a macroreticular, sulfonated, crosslinked copolymer of styrene and divinyl benzene; and the like, or combinations thereof.

In an embodiment, $H_2S$ and a feedstock comprising one or more branched $C_{10}$ monoolefins can be reacted in the presence of an acid catalyst in a continuous reactor, such as for example continuous flow reactor, continuous stirred reactors, fixed bed reactors, packed bed reactors, and the like, or combinations thereof.

In embodiments where $H_2S$ and a feedstock comprising one or more branched $C_{10}$ monoolefins are reacted in the presence of an acid catalyst in a continuous reactor, the continuous reactor can be characterized by a weight hourly space velocity (WHSV) of from about 0.1 $h^{-1}$ to about 5 $h^{-1}$, alternatively from about 0.5 $h^{-1}$ to about 4 $h^{-1}$, or alternatively from about 1 $h^{-1}$ to about 3 $h^{-1}$, based on mass of olefin per mass of catalyst per hour.

In an embodiment, $H_2S$ and a feedstock comprising one or more branched $C_{10}$ monoolefins can be reacted in the presence of an acid catalyst at a temperature of from about 100° C. to about 300° C., alternatively from about 120° C. to about 220° C., or alternatively from about 180° C. to about 200° C.

In an embodiment, $H_2S$ and a feedstock comprising one or more branched $C_{10}$ monoolefins can be reacted in the presence of an acid catalyst at a $H_2S$ to olefin molar ratio of from about 1:1 to about 10:1, alternatively from about 2:1 to about 7.5:1, or alternatively from about 2.5:1 to about 5:1.

In an embodiment, the process can comprise reacting $H_2S$ and a feedstock comprising one or more branched $C_{10}$ monoolefins in the presence of an acid catalyst to produce a crude composition (wherein the crude composition comprises from 50-100 wt. % $C_{10}$ mercaptans, alternatively from 50-90 wt. % $C_{10}$ mercaptans, alternatively from 75-85 wt. % $C_{10}$ mercaptans); wherein the $C_{10}$ mercaptans comprise from about 0 wt. % to about 5 wt. % alternatively from about 0.1 wt. % to about 4 wt. %, or alternatively from about 0.5 wt. % to about 2.5 wt. % $C_{10}$ primary mercaptans; from about 80 wt. % to about 95 wt. %, alternatively from about 82.5 wt. % to about 92.5 wt. %, or alternatively from about 85 wt. % to about 90 wt. % $C_{10}$ secondary mercaptans; and from about 5 wt. % to about 20 wt. %, alternatively from about 7.5 wt. % to about 17.5 wt. %, or alternatively from about 10 wt. % to about 15 wt. % $C_{10}$ tertiary mercaptans.

In an embodiment, the process can comprise reacting $H_2S$ and a feedstock (e.g., a first or second feedstock as described herein) comprising one or more branched $C_{10}$ monoolefins in the presence of an initiating agent to produce a crude composition; wherein the initiating agent comprises a hydrodesulfurization (HDS) catalyst.

In an embodiment, the HDS catalyst comprises a comprises a metal, a transition metal, Ru, Co, Mo, Ni, W, sulfides thereof, disulfides thereof, and the like, or combinations thereof.

In an embodiment, the HDS catalyst can be Haldor Topsoe TK-554 or TK-570, and the like, or combinations thereof.

In an embodiment, the HDS catalyst can further comprise a support, such as for example alumina, silica, and the like, or combinations thereof.

In an embodiment, $H_2S$ and a feedstock comprising one or more branched $C_{10}$ monoolefins can be reacted in the presence of an HDS catalyst in a continuous reactor, such as for example continuous flow reactor, continuous stirred reactors, fixed bed reactors, packed bed reactors, and the like, or combinations thereof.

In embodiments where $H_2S$ and a feedstock comprising one or more branched $C_{10}$ monoolefins are reacted in the presence of an HDS catalyst in a continuous reactor, the continuous reactor can be characterized by a WHSV of from about 0.1 $h^{-1}$ to about 5 $h^{-1}$, alternatively from about 0.5 $h^{-1}$ to about 4 $h^{-1}$, or alternatively from about 1 $h^{-1}$ to about 3 $h^{-1}$, based on mass of olefin per mass of catalyst per hour.

In an embodiment, $H_2S$ and a feedstock comprising one or more branched $C_{10}$ monoolefins can be reacted in the presence of an HDS catalyst at a temperature of from about 100° C. to about 300° C., alternatively from about 120° C. to about 220° C., or alternatively from about 180° C. to about 200° C.

In an embodiment, $H_2S$ and a feedstock comprising one or more branched $C_{10}$ monoolefins can be reacted in the presence of an HDS catalyst at a $H_2S$ to olefin molar ratio of from about 1:1 to about 10:1, alternatively from about 2:1 to about 7.5:1, or alternatively from about 2.5:1 to about 5:1.

In an embodiment, the process can comprise reacting $H_2S$ and a feedstock comprising one or more branched $C_{10}$ monoolefins in the presence of an HDS catalyst to produce a crude composition (wherein the crude composition comprises from 50-100 wt. % $C_{10}$ mercaptans, alternatively from 50-90 wt. % $C_{10}$ mercaptans, alternatively from 75-85 wt. % $C_{10}$ mercaptans); wherein the $C_{10}$ mercaptans comprise from about 5 wt. % to about 30 wt. % alternatively from about 10 wt. % to about 25 wt. %, or alternatively from about 15 wt. % to about 20 wt. % $C_{10}$ primary mercaptans; from about 60 wt. % to about 75 wt. %, alternatively from about 62.5 wt. % to about 72.5 wt. %, or alternatively from about 65 wt. % to about 70 wt. % $C_{10}$ secondary mercaptans; and from about 5 wt. % to about 15 wt. %, alternatively from about 7.5 wt. % to about 13.5 wt. %, or alternatively from about 9 wt. % to about 12 wt. % $C_{10}$ tertiary mercaptans.

As noted previously, any such feedstocks comprising one or more branched $C_{10}$ monoolefins can be reacted with hydrogen sulfide ($H_2S$) in the presence of an initiating agent to produce a crude composition, and the crude composition can be further refined (e.g., distilled or otherwise separated into one or more fractions such as lights, intermediate, and heavies) to yield the various compositions described herein. As described in more detail herein, the type and/or amounts of the constituent components that form the crude composition can vary depending upon the feedstock (e.g., the amount and types of olefins therein), the reaction conditions, the catalysts employed, etc., and one skilled in the art can tailor the post reactor processing of the crude composition to account for the specific compounds present in a given crude composition to yield various desired products and compositions of the types described herein.

Upon completion of the reaction of a feedstock comprising one or more branched $C_{10}$ monoolefins with hydrogen sulfide ($H_2S$), a reactor effluent can be recovered from the reactor and $H_2S$ removed therefrom to yield a crude composition. The term "crude composition" or "crude product" refers to an unrefined effluent stream recovered from the reactor after removal of $H_2S$, and in particular to an $H_2S$-free effluent stream that has not undergone any additional post-reactor processing such as flashing, distillation, or other separation techniques or processes to remove any components from the effluent stream other than the initial removal of $H_2S$.

Hydrogen sulfide ($H_2S$) is a highly corrosive, poisonous, flammable, explosive gas. As such, it is typically removed before the crude composition can be further processed or utilized. Bulk $H_2S$ can be removed under conditions of low pressure, and residual $H_2S$ can be removed at reduced temperature and pressure without removing any substantial quantities of the lights. Alternatively, $H_2S$ can also be removed by sparging inert gas into the liquid phase. Alternatively, there are other methods for removing $H_2S$ (i.e., absorption, stripping, etc.) that are known to those of skill in the art. In an embodiment, under appropriate conditions, a reactor effluent can be treated to remove essentially all of any excess and/or unreacted hydrogen sulfide ($H_2S$).

The crude composition comprises branched $C_{10}$ mercaptans and branched $C_{20}$ sulfides formed by the reaction of $H_2S$ and the one or more branched $C_{10}$ monoolefins, and the structures of these branched $C_{10}$ mercaptans and branched $C_{20}$ sulfides are described in more detail herein. In addition to branched $C_{10}$ mercaptans and branched $C_{20}$ sulfides, the crude composition can comprise a number of other compounds such as unreacted olefins, inert compounds (e.g., alkanes), non-branched $C_{10}$ mercaptans, non-branched $C_{20}$ sulfides, non-$C_{10}$ mercaptans, non-$C_{20}$ sulfides, and other impurities. The constituent components contained within the crude composition can vary depending upon the composition of the feedstock (e.g., an unpurified first feedstock as compared to a purified second feedstock as described herein) as well as reaction conditions, catalyst, etc. In various embodiments, a crude composition can comprise light, intermediate, and heavy fractions as described herein.

In an embodiment, the crude compositions can contain a variety of other non-$C_{10}$ mercaptan and non-$C_{20}$ sulfides components (e.g., impurities) such as $C_8$ mercaptans; $C_{12}$ mercaptans; $C_{14}$ mercaptans; $C_{16}$ mercaptans; $C_{18}$ mercaptans; $C_{16-36}$ sulfides represented by the structure $R^3$—S—$R^4$, wherein $R^3$ and $R^4$ are each independently a functional group derived from an olefin selected from the group consisting of $C_8$ monoolefins, $C_{10}$ monoolefins, $C_{12}$ monoolefins, $C_{14}$ monoolefins, $C_{16}$ monoolefins, and $C_{18}$ monoolefins, wherein $R^3$ and $R^4$ are not both branched $C_{10}$ monoolefins; unreacted $C_{8-18}$ monoolefins; non-olefin impurities selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate; and combinations thereof.

In an embodiment, a crude composition comprising branched $C_{10}$ mercaptans and branched $C_{20}$ sulfides can be separated by any process or unit operation known in the art. For example, a crude composition can be processed (e.g., distilled) to remove a fraction of light compounds. Alternatively, a crude composition can be processed to recover both a lights fraction and an intermediates fraction (e.g., a rough cut), followed by further processing to obtain one or more fine cuts. Alternatively, a crude composition can be processed to recover a heavies fraction (e.g., a $C_{20}$ sulfide fraction). Alternatively, a crude composition can be processed to separate out any combination of a lights fraction, an intermediates fraction (e.g., comprising $C_{10}$ mercaptans, including branched $C_{10}$ mercaptans), and a heavies fraction (e.g., comprising $C_{20}$ sulfides, including branched $C_{20}$ sulfides). Furthermore, a light, intermediate or heavy fraction (e.g., a rough cut) can be further processed or parsed to obtain one or more desired fine cuts (e.g., a $C_{10}$ mercaptan fraction). Alternatively, a crude composition can be separated to produce a high-purity $C_{10}$ mercaptan stream and/or a high-purity $C_{20}$ sulfide stream (e.g., to obtain a desired fine cut or fraction such as a $C_{10}$ mercaptan fraction). Further, these separated streams can be blended in any combination of ratios to produce a mixture with specific concentrations of one of more components (e.g., desired blend ratios of branched $C_{10}$ mercaptans and/or branched $C_{20}$ sulfides, for example to aid in a particular end use). The unit operations/ processes used for these separations are known to one of skill and the art and include, but are not limited to, distillation, fractionation, flashing, stripping, and absorption, and others. The unit operation conditions, such as for example, temperature, pressure, flow rates, and others at which these unit operations produce one or more of the desired fractions can easily be determined by one of ordinary skill in the art.

In an embodiment, a lights fraction is removed from the crude composition, for example by flashing, distillation, fractionation, stripping, absorption, etc.

In an embodiment, the lights fraction can comprise at least about 90 wt. %, alternatively at least about 90 wt. %, alternatively at least about 95 wt. %, alternatively at least about 96 wt. %, alternatively at least about 97 wt. %, alternatively at least about 98 wt. %, alternatively at least about 99 wt. % $C_{9-}$ compounds, based on the total weight of the lights fraction. Nonlimiting examples of $C_{9-}$ compounds include $C_{9-}$ monoolefins (e.g., unreacted $C_{9-}$ monoolefins), $C_{9-}$ mercaptans, $C_{9-}$ alkanes, cyclohexane, methylcyclopentane, methylcyclohexane, benzene, toluene, ethylbenzene, xylene, mesitylene, $C_{9-}$ alcohols, 2-ethyl-1-hexanol, and the like, or combinations thereof. In an embodiment, the lights fraction can comprise less than about 10 wt. %, alternatively less than about 5 wt. %, alternatively less than about 4 wt. %, alternatively at less than about 3 wt. %, alternatively less than about 2 wt. %, alternatively less than about 1 wt. % $C_{10+}$ compounds, based on the total weight of the lights fraction.

In an embodiment, the $C_{9-}$ monoolefins can comprise, can consist essentially of, or can be, a $C_7$ monoolefin, a $C_8$ monoolefin, a $C_9$ monoolefin, or combinations thereof; alternatively, a $C_7$ monoolefin; alternatively, a $C_8$ monoolefin; or alternatively, a $C_9$ monoolefin. In some embodiments, the $C_{9-}$ monoolefins can comprise, can consist essentially of, or can be, a $C_8$ monoolefin (e.g., 1-octene).

In an embodiment, the $C_{9-}$ mercaptans can comprise, can consist essentially of, or can be, a $C_7$ mercaptan, a $C_8$ mercaptan, a $C_9$ mercaptan, or combinations thereof; alternatively, a $C_7$ mercaptan; alternatively, a $C_8$ mercaptan; or alternatively, a $C_9$ mercaptan. In some embodiments, the $C_{9-}$ mercaptans can comprise, can consist essentially of, or can be, a $C_8$ mercaptan.

Following removal of the lights (for example, via flash), a combined intermediate and heavy fraction (i.e., $C_{10+}$ compounds sometimes referred to as a kettle product) can remain, and the combined intermediate and heavy fraction can be used "as is" or can be further processed, for example separated or split into separate intermediate and heavy fractions (and said separate intermediate and heavy fractions can be subsequently recombined in various blends and associated blend ratios), as described in more detail herein. In an embodiment, a combined intermediate and heavy fraction (i.e., $C_{10+}$ compounds) formed by removal of the lights fraction from the crude composition can comprise less than about 15 wt. %, alternatively less than about 10 wt. %, alternatively less than about 9 wt. %, alternatively less than about 8 wt. %, alternatively less than about 7 wt. %, alternatively less than about 6 wt. %, alternatively less than about 5 wt. %, alternatively less than about 4 wt. %, alternatively less than about 3 wt. %, alternatively less than about 2 wt. %, alternatively less than about 1 wt. % $C_{9-}$ products, based on the total weight of the combined intermediate and heavy fraction (i.e., $C_{10+}$ compounds).

In an embodiment, a combined intermediate and heavy fraction (i.e., $C_{10+}$ compounds) can comprise (A) at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) at least about 10 wt. %, alternatively at least about 15 wt. %, alternatively at least about 20 wt. %, alternatively at least about 25 wt. % sulfides, or alternatively at least about 30 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, the crude composition can be flashed to remove a lights fraction as described herein to produce a combined intermediate and heavy fraction (i.e., $C_{10+}$ compounds) comprising: (A) at least about 25, 30, 35, 40, 45, 50, 55, 60, 65, 70, 75, 80, or 85 wt. % $C_{10}$ branched mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) at least about 5 wt. %, alternatively at least about 10 wt. %, alternatively at least about 15 wt. %, alternatively at least about 20 wt. %, alternatively at least about 25 wt. %, or alternatively at least about 30 wt. % branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, the crude composition can be flashed to remove a lights fraction as described herein to produce a combined intermediate and heavy fraction (i.e., $C_{10+}$ compounds) comprising: (A) from at least about 50 wt. % to at least about 90 wt. %, alternatively from at least about 55 wt. % to at least about 85 wt. %, or alternatively from at least about 60 wt. % to at least about 80 wt. % mercaptans, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof and (B) from at least about 10 wt. % to at least about 30 wt. %, alternatively from at least about 10 wt. % to at least about 25 wt. %, alternatively from at least about 12.5 wt. % to at least about 22.5 wt. %, or alternatively from at least about 15 wt. % to at least about 20 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, the crude composition can be flashed to remove a lights fraction and subsequently further separated to produce an intermediate fraction and a heavies fraction. The intermediate fraction and the heavies fractions can then be optionally further processed (e.g., polished) and mixed in any appropriate ratio to produce a blended composition comprising: (A) at least about 25 wt. %, alternatively at least about 30 wt. %, alternatively at least about 40 wt. %, alternatively at least about 50 wt. %, alternatively at least about 80 wt. %, or alternatively at least about 90 wt. % $C_{10}$ mercaptans (e.g., branched $C_{10}$ mercaptans) selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; (B) at least about 5 wt. %, alternatively at least about 10 wt. %, alternatively at least about 15 wt. %, alternatively at least about 20 wt. %, alternatively at least about 25 wt. %, or alternatively at least about 30 wt. % $C_{20}$ sulfides (e.g., branched $C_{20}$ sulfides) represented by structure $R^1$—S—$R^2$, wherein $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof; and one or more of the following components (C)-(I): (C) less than about 5 wt. %, alternatively less than about 4 wt. %, alternatively less than about 3 wt. %, alternatively less than about 2 wt. %, or alternatively less than about 1 wt. % $C_8$ mercaptans; (D) less than about 15 wt. %, alternatively less than about 10 wt. %, or alternatively less than about 5 wt. % $C_{12}$ mercaptans; (E) less than about 15 wt. %, alternatively less than about 10 wt. %, or alternatively less than about 5 wt. % $C_{14}$ mercaptans; (F) less than about 5 wt. %, alternatively less than about 4 wt. %, alternatively less than about 3 wt. %, alternatively less than about 2 wt. %, or alternatively less than about 1 wt. % $C_{16}$ mercaptans and/or $C_{18}$ mercaptans; (G) less than about 1 wt. %, alternatively less than about 0.5 wt. %, alternatively less than about 0.4 wt. %, alternatively less than about 0.3 wt. %, alternatively less than about 0.2 wt. %, or alternatively less than about 0.1 wt. % $C_{16-36}$ sulfides represented by the structure $R^3$—S—$R^4$, wherein $R^3$ and $R^4$ are each independently a functional group derived from an olefin selected from the group consisting of $C_8$ monoolefins, $C_{10}$ monoolefins, $C_{12}$ monoolefins, $C_{14}$ monoolefins, $C_{16}$ monoolefins, and $C_{18}$ monoolefins, wherein $R^3$ and $R^4$ are not both branched $C_{10}$ monoolefins; (H) less than about 10 wt. %, alternatively less than about 5 wt. %, alternatively less than about 4 wt. %, alternatively less than about 3 wt. %, alternatively less than about 2 wt. %, or alternatively less than about 1 wt. % unreacted $C_{8-18}$ monoolefins; and (I) less than about 10 wt. %, alternatively less than about 5 wt. %, alternatively less than about 4 wt. %, alternatively less than about 3 wt. %, alternatively less than about 2 wt. %, or alternatively less than about 1 wt. % non-olefin impurities selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate. In various embodiments, the blended composition can comprise varying amounts of each of components (C)-(I), and the presence of each component (C)-(I) and the amount thereof can be independently formulated and/or controlled. In various embodiments, the blended composition can comprise an amount of one or more components (C)-(I) that is greater than zero (i.e., above a detection limit associated with the component) and less than the upper range endpoint set forth above (e.g., component (C) is present in the composition in an amount greater than zero and less than about 5 wt. %, and so forth as set forth above).

In some embodiments, a mercaptan/sulfide composition of the type disclosed herein can be prepared by combining at least a portion of a first mercaptan/sulfide composition (wherein only a lights fraction has been removed from the crude product to yield a combined intermediate and heavy fraction, e.g., $C_{10+}$ compounds) with at least a portion of a heavies fraction comprising a sulfide composition to yield a second mercaptan/sulfide composition, wherein a sulfide content of the second mercaptan/sulfide composition is greater than a sulfide content of the first mercaptan/sulfide composition.

In an embodiment, the crude can be separated into light, intermediate, and heavy fractions by distillation, for example in a single distillation column having a light fraction recovered as an overhead stream, an intermediate fraction (e.g., comprising branched $C_{10}$ mercaptans) recovered as a side stream, and a heavy fraction (e.g., comprising branched $C_{20}$ sulfides) recovered as a bottom stream. In alternative embodiments, the separation can be in sequential steps such as removal of the lights fraction in a first distillation column, followed by separation of the intermediate fraction (e.g., comprising branched $C_{10}$ mercaptans) as an overhead stream in a second distillation column and the heavy fraction (e.g., comprising $C_{11+}$ compounds, including branched $C_{20}$ sulfides) as a bottom stream of the second distillation column. These "rough-cut" light, intermediate, and heavy streams can be used "as is" or they can be further processed (e.g., further refined or polished, for example by additional distillation or other separation techniques to produce "fine-cuts") and/or blended to obtain a variety of products that are salable or otherwise available for a variety of end uses such as mining ore collector compositions or chain transfer agents. For example, a variety of mercaptan compositions, sulfide compositions, and mixed mercaptan/sulfide compositions can be produced of the type disclosed in more detail herein.

In an embodiment, an intermediate fraction can comprise at least about 25 wt. %, alternatively at least about 30 wt. %, alternatively at least about 40 wt. %, alternatively at least about 50 wt. % branched $C_{10}$ mercaptans, alternatively at least about 75 wt. % branched $C_{10}$ mercaptans, or alternatively at least about 85 wt. % branched $C_{10}$ mercaptans. In such embodiment, the branched $C_{10}$ mercaptans can be selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In an embodiment, the heavy fraction can comprise at least about 5, 10, 15, 20, 25, 30, 35, 40, 45, 50, 55, 60, 65, 70, 75, 80, or 85 wt. %, branched $C_{20}$ sulfides represented by structure $R^1$—S—$R^2$, wherein both $R^1$ and $R^2$ are each independently a branched $C_{10}$ alkyl group derived from the branched $C_{10}$ monoolefin, and wherein the branched $C_{10}$ alkyl group is selected from the group consisting of

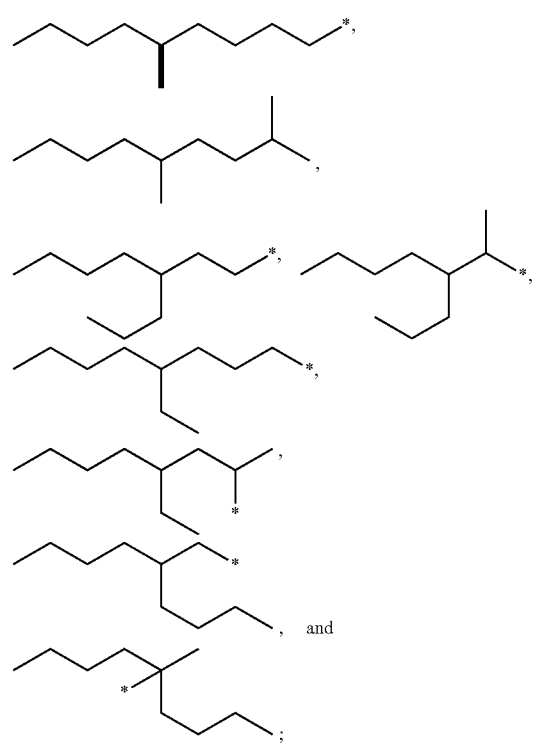

wherein * designates the attachment point to the S atom of the branched $C_{20}$ sulfide.

In an embodiment, a mercaptan composition can comprise mercaptans, wherein at least a portion of the mercaptans comprise $C_{10}$ mercaptans, and wherein at least a portion of the $C_{10}$ mercaptans comprise branched $C_{10}$ mercaptans. In an embodiment, the branched $C_{10}$ mercaptans can comprise 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), or combinations thereof.

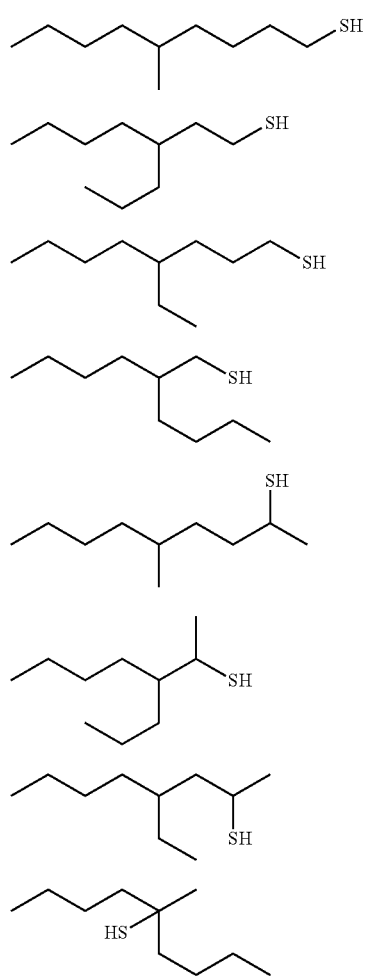

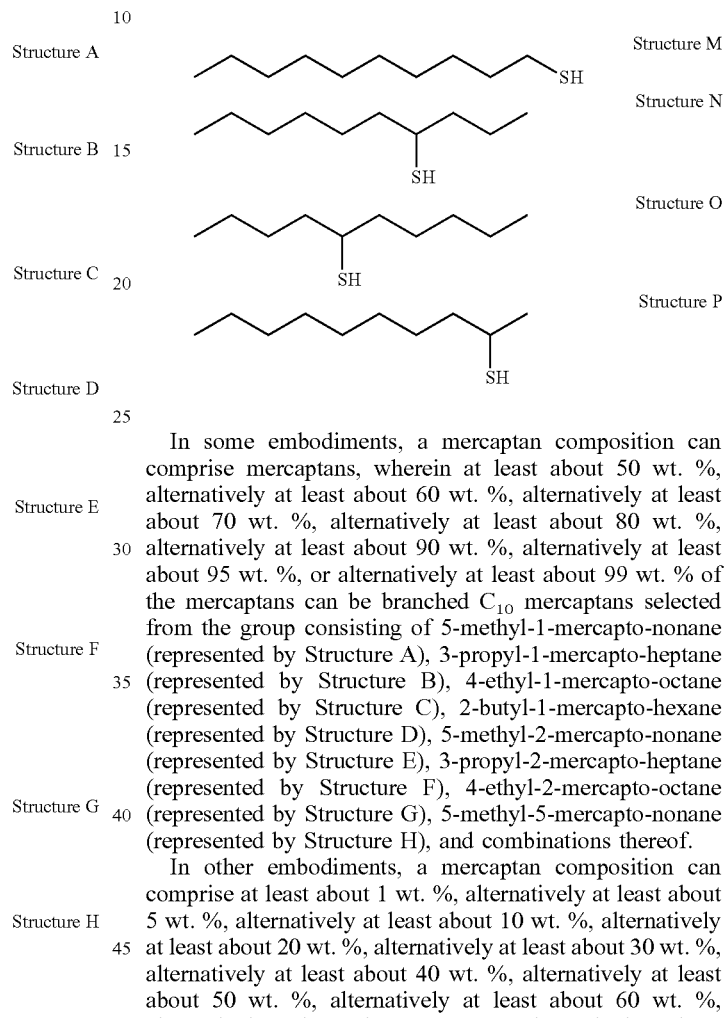

For purposes of the disclosure herein, branched $C_{10}$ mercaptans refer to mercaptans (or thiols) that are characterized by the general formula R—SH, wherein R is a branched alkyl group (as opposed to a linear alkyl group), i.e., an alkyl group substituted with alkyl substituents; and wherein R has a total of 10 carbon atoms. Further, for purposes of the disclosure herein, a composition comprising mercaptans, wherein at least a portion of the mercaptans are branched $C_{10}$ mercaptans (e.g., 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), or combinations thereof), can also be referred to as a "branched $C_{10}$ mercaptan composition." In an embodiment, the mercaptan composition can comprise any suitable amount of branched $C_{10}$ mercaptans.

In an embodiment, the $C_{10}$ mercaptans can further comprise non-branched $C_{10}$ mercaptans, such as for example 1-mercapto-decane (represented by Structure M), 4-mercapto-decane (represented by Structure N), 5-mercapto-decane (represented by Structure O), 2-mercapto-decane (represented by Structure P), or combinations thereof.

In some embodiments, a mercaptan composition can comprise mercaptans, wherein at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In other embodiments, a mercaptan composition can comprise at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans, wherein at least a portion of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In yet other embodiments, a mercaptan composition can comprise at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans; wherein at least 50 wt. %, alternatively at least about 60 wt. %, alternatively at least about 70 wt. %, alternatively at least about 75 wt. %, alternatively at least about 80 wt. %, or alternatively at least 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In yet other embodiments, a mercaptan composition can comprise at least about 50, 55, 60, 65, 70, 75, 80, 85, 90, 95, or 99 wt. % mercaptans; wherein at least about 25, 30, 35, 40, 45, 50, 55, 60, 65, 70, 75, 80, 85, 90, 95, or 99 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a mercaptan composition can comprise from at least about 50 wt. % to at least about 90 wt. %, alternatively from at least about 55 wt. % to at least about 85 wt. %, or alternatively from at least about 60 wt. % to at least about 80 wt. % mercaptans, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a mercaptan composition can consist of or consist essentially of branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a mercaptan composition can comprise at least about 1, 5, 10, 15, 20, 25, 30, 35, 40, 45, 50, 55, 60, 65, 70, 75, 80, 85, 90, 95, or 99 wt. % branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a composition can comprise mercaptans, wherein at least about 50, 55, 60, 65, 70, 75, 80, 85, 90, 95, or 99 wt. % of the mercaptans are branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In an embodiment, a sulfide composition can comprise sulfides, wherein at least a portion of the sulfides comprise $C_{20}$ sulfides, and wherein at least a portion of the $C_{20}$ sulfides comprise branched $C_{20}$ sulfides represented by structure $R^1$—S—$R^2$, wherein $R^1$ and $R^2$ can each independently be an alkyl group, and wherein at least a portion of the alkyl groups comprises a branched $C_{10}$ alkyl group. In an embodiment, the alkyl group (e.g., a branched $C_{10}$ alkyl group as $R^1$, $R^2$) can comprise a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

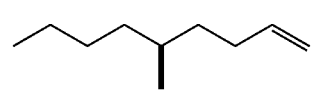

Structure I

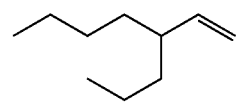

Structure J

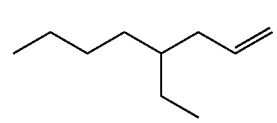

Structure K

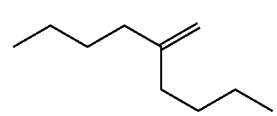

Structure L

For purposes of the disclosure herein a sulfide will be referred to by the total number of carbon atoms (as opposed to the number of carbons of only one of the alkyl groups present in a dialkyl sulfide). For example, a $H_{21}C_{10}$—S—$C_{10}H_{21}$ sulfide will be referred to as a $C_{20}$ sulfide (rather than a $C_{10}$ sulfide). For purposes of the disclosure herein, branched $C_{20}$ sulfides refer to sulfides (or thioethers) that are characterized by the general formula $R^1$—S—$R^2$, wherein both $R^1$ and $R^2$ are each independently a branched $C_{10}$ alkyl group (as opposed to a linear alkyl group), i.e., an alkyl group substituted with alkyl substituents. Stated alternatively, branched $C_{20}$ sulfides refer to sulfides wherein both $R^1$ and $R^2$ are branched $C_{10}$ alkyl groups, wherein $R^1$ and $R^2$ can be the same or different. Further, for purposes of the disclosure herein, a composition comprising sulfides, wherein at least a portion of the sulfides are branched $C_{20}$ sulfides represented by structure $R^1$—S—$R^2$, wherein both $R^1$ and $R^2$ are each independently an alkyl group, wherein at least a portion of the alkyl group comprises a branched $C_{10}$ alkyl group (e.g., a functional group derived from an olefin, and wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof), can also be referred to as a "branched $C_{20}$ sulfide composition." In an embodiment, the sulfide composition can comprise any suitable amount of branched $C_{20}$ sulfides.

In an embodiment, a sulfide composition can comprise sulfides, wherein at least a portion of the sulfides comprise $C_{20}$ sulfides, and wherein at least a portion of the $C_{20}$ sulfides comprise branched $C_{20}$ sulfides represented by structure $R^1$—S—$R^2$, wherein both $R^1$ and $R^2$ can each independently be a branched $C_{10}$ alkyl group derived from a branched $C_{10}$ monoolefin, and wherein the branched $C_{10}$ alkyl group is selected from the group consisting of

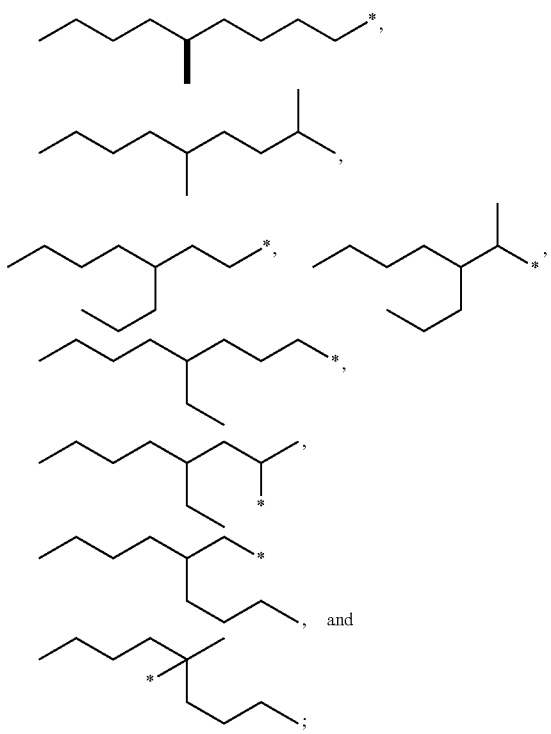

wherein * designates the attachment point to the S atom of the branched $C_{20}$ sulfide. In an embodiment, the branched $C_{10}$ monoolefin can comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof. Generally, a monoolefin is a linear or branched aliphatic hydrocarbon olefin that has one and only one carbon-carbon double bond. Generally, a $C_n$ monoolefin is a linear or branched aliphatic hydrocarbon olefin that has n and only n carbon atoms, and one and only one carbon-carbon double bond. A $C_{10}$ monoolefin is a linear or branched aliphatic hydrocarbon olefin that has ten and only ten carbon atoms, and one and only one carbon-carbon double bond. A branched $C_{10}$ monoolefin is a branched aliphatic hydrocarbon olefin that has ten and only ten carbon atoms, and one and only one carbon-carbon double bond.

In an embodiment, the $C_{20}$ sulfides can further comprise non-branched $C_{20}$ sulfides and/or partially branched $C_{20}$ sulfides represented by structure $R^1$—S—$R^2$, wherein both $R^1$ and $R^2$ (in the case of non-branched $C_{20}$ sulfides) or one of the $R^1$ and $R^2$ (in the case of partially-branched $C_{20}$ sulfides) can be a linear $C_{10}$ alkyl group derived from a linear $C_{10}$ monoolefin, such as for example 4-decene (represented by Structure Q), 5-decene (represented by Structure R), 1-decene (represented by Structure S), or combinations thereof.

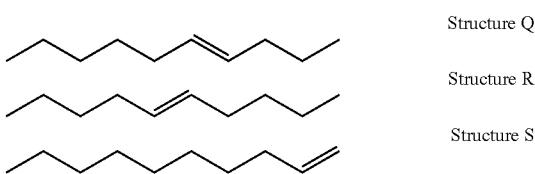

For purposes of the disclosure herein, the non-branched $C_{20}$ sulfides represented by structure $R^1$—S—$R^2$ are the sulfides wherein both $R^1$ and $R^2$ are each independently a linear $C_{10}$ alkyl group derived from a linear $C_{10}$ monoolefin. Further, for purposes of the disclosure herein, the partially branched $C_{20}$ sulfides represented by structure $R^1$—S—$R^2$ are the sulfides wherein one of the $R^1$ and $R^2$ is a linear $C_{10}$ alkyl group derived from a linear $C_{10}$ monoolefin, while the other one of the $R^1$ and $R^2$ is a branched $C_{10}$ alkyl group derived from a branched $C_{10}$ monoolefin as described herein.

In some embodiments, a sulfide composition can comprise sulfides, wherein at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In other embodiments, a sulfide composition can comprise at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % sulfides, wherein at least a portion of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In other embodiments, a sulfide composition can comprise at least about 1, 5, 10, 15, 20, 25, 30, 35, 40, 45, 50, 55, 60, 65, 70, 75, 80, 85, 90, 95, or 99 wt. %, sulfides, wherein at least about 1, 5, 10, 15, 20, 25, 30, 35, 40, 45, 50, 55, 60, 65, 70, 75, 80, 85, 90, 95, or 99 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In yet other embodiments, a sulfide composition can comprise at least about 10 wt. %, alternatively at least about 15 wt. %, alternatively at least about 20 wt. %, or alternatively at least about 25 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition can comprise from at least about 10 wt. % to at least about 30 wt. %, alternatively from at least about 12.5 wt. % to at least about 22.5 wt. %, or alternatively from at least about 15 wt. % to at least about 20 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition can consist of or consist essentially of branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition can comprise at least about 5 wt. %, alternatively at least about 10 wt. %, alternatively at least about 15 wt. %, or alternatively at least about 20 wt. % $C_{20}$ sulfides (e.g., branched $C_{20}$ sulfides) represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition comprises at least about 1, 5, 10, 15, 20, 25, 30, 35, 40, 45, 50, 55, 60, 65, 70, 75, 80, 85, 90, 95, or 99 wt. % branched $C_{20}$ sulfides represented by the structure $R^1$—S—$R^2$, wherein $R^1$ and $R^2$ are each independently a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, a mercaptan/sulfide composition can comprise one or more mercaptans and one or more sulfides of the type disclosed herein. For purposes of the disclosure herein, a composition comprising (i) mercaptans, wherein at least a portion of the mercaptans are branched $C_{10}$ mercaptans, and (ii) sulfides, wherein at least a portion of the sulfides are branched $C_{20}$ sulfides, can also be referred to as a "branched $C_{10}$ mercaptan/$C_{20}$ sulfide composition." In an embodiment, the mercaptan/sulfide composition can comprise any suitable amount of branched $C_{10}$ mercaptans, and any suitable amount of branched $C_{20}$ sulfides.

In an embodiment, a mercaptan/sulfide composition can comprise (A) at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans, wherein at least a portion of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % sulfides, wherein at least a portion of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, a mercaptan/sulfide composition can comprise $C_{10}$ mercaptans represented by the general formula R—SH and/or $C_{20}$ sulfides represented by structure $R^1$—S—$R^2$ that are formed by reacting an olefin feedstock comprising olefins with $H_2S$ as described in more detail herein, wherein the olefins present in the olefin feedstock provide the alkyl group represented by R, $R^1$, and $R^2$. In such embodiments, the R group of the $C_{10}$ mercaptans and/or the $R^1$ and $R^2$ groups of the $C_{20}$ sulfides are provided by or derived from the counterpart R, $R^1$, and $R^2$ groups present in the olefins in the olefin feedstock. In an embodiment, R, $R^1$ and $R^2$ can each independently be an alkyl group, wherein at least a portion of the alkyl groups can comprise a functional group derived from an olefin, wherein the olefin is present in a feedstock (e.g., a first feedstock as described herein) comprising a) at least about 76 mol %, alternatively at least about 78 mol %, alternatively at least about 80 mol %, or alternatively at least about 82 mol % $C_{10}$ monoolefins; and b) at least about 1 mol %, alternatively at least about 2 mol %, alternatively at least about 3 mol %, or alternatively at least about 4 mol % $C_{14}$ monoolefins. In such embodiment, the $C_{10}$ monoolefins can comprise i) at least about 3 mol %, alternatively at least about 4 mol %, alternatively at least about 5 mol %, alternatively at least about 6 mol %, alternatively at least about 7 mol %, or alternatively at least about 8 mol % 2-butyl-1-hexene (represented by Structure L), ii) at least about 8 mol %, alternatively at least about 9 mol %, alternatively at least about 10 mol %, alternatively at least about 11 mol %, alternatively at least about 12 mol %, or alternatively at least about 13 mol % 3-propyl-1-heptene (represented by Structure J), iii) at least about 6 mol %, alternatively at least about 7 mol %, alternatively at least about 8 mol %, alternatively at least about 9 mol %, alternatively at least about 10 mol %, or alternatively at least about 11 mol % 4-ethyl-1-octene (represented by Structure K), and iv) at least about 20 mol %, alternatively at least about 22 mol %, alternatively at least about 24 mol %, alternatively at least about 26 mol %, alternatively at least about 28 mol %, or alternatively at least about 30 mol % 5-methyl-1-nonene (represented by Structure I). In an embodiment, the $C_{10}$ monoolefins can comprise from about 1 mol % to about 16 mol %, alternatively from about 2 mol % to about 15 mol %, alternatively from about 3 mol % to about 14 mol %, alternatively from about 4 mol % to about 13 mol %, or alternatively from about 6 mol % to about 12 mol % 4-decene and/or 5-decene. In an embodiment, the $C_{10}$ monoolefins can comprise from about 0.5 mol % to about 9 mol %, alternatively from about 1 mol % to about 8 mol %, alternatively from about 1.5 mol % to about 7 mol %, or alternatively from about 2 mol % to about 6 mol % 1-decene.

In an embodiment, the olefin (e.g., corresponding to R, $R^1$ or $R^2$) present in the olefin feedstock (e.g., a first feedstock as described herein) can further comprise from about 0.1 mol % to about 5 mol %, alternatively from about 0.25 mol % to about 4 mol %, or alternatively from about 0.5 mol % to about 3 mol % $C_{12}$ monoolefins. In such embodiment, the $C_{12}$ monoolefins can comprise from about 54 mol % to about 74 mol %, alternatively from about 56 mol % to about 72 mol %, alternatively from about 58 mol % to about 70 mol %, or alternatively from about 60 mol % to about 68 mol % 1-dodecene.

In an embodiment, the olefin (e.g., corresponding to R, $R^1$ or $R^2$) present in the olefin feedstock (e.g., a first feedstock as described herein) can further comprise from about 0.1 mol % to about 5 mol %, alternatively from about 0.25 mol % to about 4 mol %, or alternatively from about 0.5 mol % to about 3 mol % $C_8$ monoolefins. In such embodiment, the $C_8$ monoolefins can comprise at least about 95 mol %, alternatively at least about 96 mol %, alternatively at least about 97 mol %, alternatively at least about 98 mol %, or alternatively at least about 99 mol % 1-octene.

In an embodiment, the olefin (e.g., corresponding to R, $R^1$ or $R^2$) present in the olefin feedstock (e.g., a first feedstock as described herein) can further comprise from about 0.05 mol % to about 2 mol %, alternatively from about 0.04 mol % to about 1.5 mol %, alternatively from about 0.06 mol % to about 1.25 mol %, alternatively from about 0.08 mol % to about 1 mol %, or alternatively from about 0.1 mol % to about 0.75 mol % $C_{16}$ monoolefins and/or $C_{18}$ monoolefins.

In an embodiment where the R group of the $C_{10}$ mercaptans and/or the $R^1$ and $R^2$ groups of the $C_{20}$ sulfides are provided by or derived from the counterpart R, $R^1$, and $R^2$ groups present in the olefins in the olefin feedstock (e.g., a first feedstock obtained from a 1-hexene process as described herein), the resultant mercaptan/sulfide composition can be a crude composition that can be further separated and refined into other compositions as described herein.

In an embodiment, mercaptan compositions, sulfide compositions, and/or mercaptan/sulfide compositions as disclosed herein advantageously display improvements in one or more composition characteristics when compared to otherwise similar compositions lacking branched $C_{10}$ mercaptans.

In an embodiment, a mercaptan composition and/or a mercaptan/sulfide composition comprising equal to or greater than about 25 wt. % $C_{10}$ branched mercaptans as disclosed herein can advantageously have an odor less unpleasant and less offensive than an odor of an otherwise similar composition comprising equal to or greater than about 25 wt. % n-decyl mercaptan, as perceived by equal to or greater than about 51% of human subjects exposed to the odor of each composition.

In an embodiment, a mercaptan composition and/or a mercaptan/sulfide composition comprising equal to or greater than about 25 wt. % $C_{10}$ branched mercaptans as disclosed herein can advantageously have an odor less unpleasant than an odor of an otherwise similar composition comprising equal to or greater than about 25 wt. % n-dodecyl mercaptan and/or tert-dodecyl mercaptan, as perceived by equal to or greater than about 51% of human subjects exposed to the odor of each composition. Additional advantages of the mercaptan compositions, sulfide compositions, and/or mercaptan/sulfide compositions and processes of producing same as disclosed herein can be apparent to one of skill in the art viewing this disclosure.

Chain Transfer Agent Compositions

Alternative embodiments of the invention also are directed to use in emulsion polymerization. It was found that the branched $C_{10}$ mercaptan compositions disclosed hereinabove are effective as chain transfer agents in emulsion polymerization reactions. The compositions useful in emulsion polymerization as chain transfer agents comprise any of the branched $C_{10}$ mercaptan compositions in any of the amounts described hereinabove. Additionally, it was unexpectedly found that compositions comprising branched $C_{10}$ mercaptans do not have an undesirable or offensive odor often associated with other mercaptans.

In various embodiments, the disclosed chain transfer agent compositions can be described as the mercaptan compositions (e.g., a composition comprising one or more branched $C_{10}$ mercaptans); an intermediate fraction; a branched $C_{10}$ mercaptan composition; or combinations thereof, as each of these terms is defined, described, and otherwise used herein.

In an embodiment, the chain transfer agent composition can comprise, consist of, or consist essentially of at least one branched $C_{10}$ mercaptan. The at least one branched $C_{10}$ mercaptan can be present in an amount of at least 30 wt. %, alternatively at least 40 wt. %, alternatively at least 50 wt. %, alternatively at least 60 wt. %, alternatively at least 70 wt. %, alternatively at least 80 wt. %, alternatively at least 85 wt. %, alternatively at least 90 wt. %, alternatively at least 95 wt. %, or alternatively at least 99 wt. % based on a total weight of the chain transfer agent composition. The branched $C_{10}$ mercaptans can be selected from 5-methyl-1-mercapto-nonane (represented by Structure A), 3-propyl-1-mercaptoheptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), or combinations thereof.

In another embodiment, the chain transfer agent composition can comprise, consist of, or consist essentially at least 85 wt. %, alternatively at least 90 wt. %, alternatively at least 95 wt. %, alternatively at least 99 wt. %, alternatively at least 99.9 wt. % $C_{10}$ to $C_{18}$ mercaptans. In such embodiments, at least 50 wt. %, alternatively at least 60 wt. %, alternatively at least 70 wt. %, alternatively at least 80 wt. %, alternatively at least 85 wt. %, alternatively at least 90 wt. %, alternatively at least 95 wt. %, or alternatively at least 99 wt. % of the $C_{10}$ mercaptan compounds are branched, and the branched $C_{10}$ mercaptans are optionally selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In additional embodiments, the chain transfer agent compositions described herein can include (A) less than about 0.01 wt. %, alternatively less than about 0.5 wt. %, alternatively less than about 1 wt. %, alternatively less than about 2 wt. %, alternatively less than about 5 wt. %, or alternatively less than about 10 wt. % $C_{16-36}$ sulfides represented by the structure $R^3$—S—$R^4$, wherein $R^3$ and $R^4$ are each independently a functional group derived from an olefin selected from the group consisting of $C_8$ monoolefins, $C_{10}$ monoolefins, $C_{12}$ monoolefins, $C_{14}$ monoolefins, $C_{16}$ monoolefins, and $C_{18}$ monoolefins, wherein $R^3$ and $R^4$ are not both branched $C_{10}$ monoolefins; (B) less than about 10 wt. %, alternatively less than about 5 wt. %, alternatively less than about 4 wt. %, alternatively less than about 3 wt. %, alternatively less than about 2 wt. %, or alternatively less than about 1 wt. % unreacted $C_{8-18}$ monoolefins; and (C) less than about 10 wt. %, alternatively less than about 5 wt. %, alternatively less than about 4 wt. %, alternatively less than about 3 wt. %, alternatively less than about 2 wt. %, or alternatively less than about 1 wt. % non-olefin components selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate.

While not wishing to be limited by theory, as described in this disclosure and as known by one of ordinary skill in the art, these and other specific compositions can be obtained any number of ways including but not limited to (A) removing $H_2S$ and distilling the light compounds from the crude reaction product, and then subsequently distilling either a purified $C_{10}$ mercaptans fraction or the $C_{10}$-$C_{17}$ intermediates fraction from the remaining reaction product; or (B) separating the light fraction, the $C_{10}$ mercaptans, the intermediate fraction, and the heavy fraction of the crude reaction mixture in any order or by any means to produce a fraction containing the chain transfer agent compositions disclosed above. In a preferred embodiment, the chain transfer agent composition can be prepared by first removing essentially all of the light fraction and the intermediate fraction (containing the $C_{10}$ to $C_{18}$ mercaptans) from the heavies fraction (containing the sulfides) in a first step (for example, in a first distillation column), followed by removing essentially all of the light fraction from the intermediate fraction (containing the $C_{10}$ to $C_{18}$ mercaptans) in a second step (for example, in a second distillation column).

In embodiments, the chain transfer agent compositions disclosed herein have an odor which is less unpleasant and/or offensive than an odor of mercaptan compounds which include n-dodecyl mercaptans, tert-dodecyl mercaptans, or combinations thereof present in an amount of equal to or greater than about 25 wt. % of the mercaptan compounds in an otherwise similar chain transfer agent composition.

The chain transfer agent compositions disclosed herein can be included as part of an emulsion polymerization mixture. In an embodiment, the amount of the chain transfer agent composition present in the emulsion polymerization mixture can be from about 0.01 wt. % to about 5 wt. %, or alternatively from about 0.03 wt. % to about 3 wt. % based on the total weight of the emulsion polymerization mixture. In a preferred embodiment, the amount of chain transfer agent added to the emulsion polymerization mixture can be from about 0.03 wt. % to about 1 wt. % based on a total weight of the emulsion polymerization mixture. In an alternative embodiment, the chain transfer agent can be added to the emulsion polymerization mixture in an amount from about 0.01 grams to about 5 grams per 100 grams of monomer, or alternatively in an amount from about 0.05 grams to about 3 grams per 100 grams of monomer. In a preferred embodiment the chain transfer agent can be added to the emulsion polymerization mixture in an amount from about 0.1 gram to about 1 gram per 100 grams of monomer.

The emulsion polymerization mixture can further include one or more monomers, one or more surfactants, one or more polymerization initiators, water, or combinations thereof.

Embodiments of the monomers suitable for use in the emulsion polymerization mixture and polymerization processes discloses herein are those commonly and normally used in free-radical emulsion polymerization reaction. For example, monomers containing vinyl unsaturation(s), and more particularly vinyl monomers, conjugated diene monomers, acrylic monomers, methacrylic monomers, and combinations thereof.

Nonlimiting embodiments of monomers include acrylic acid, alkyl acrylates, methacrylic acid, alkyl methacrylates, conjugated dienes, styrene, styrene derivatives, acrylamide, acrylonitrile, and combinations thereof. Nonlimiting examples of these monomers include alkyl acrylates include ethyl acrylate, ethyl acrylate, n-propyl acrylate, iso-propyl acrylate, n-butyl acrylate, iso-butyl acrylate, tert-butyl acrylate, n-pentyl acrylate, neo-pentyl acrylate, iso-amyl acrylate, n-hexyl acrylate, iso-hexyl acrylate, cyclohexyl acrylate, iso-octyl acrylate, 2-ethylhexyl acrylate, decyl acrylate, iso-decyl acrylate, lauryl acrylate, stearyl acrylate and iso-bornyl acrylate, methyl methacrylate, ethyl methacrylate, n-propyl methacrylate, iso-propyl methacrylate, n-butyl methacrylate, iso-butyl methacrylate, tert-butyl methacrylate, n-pentyl methacrylate, neo-pentyl methacrylate, iso-amyl methacrylate, n-hexyl methacrylate, iso-hexyl methacrylate, cyclohexyl methacrylate, iso-octyl methacrylate, 2-ethylhexyl methacrylate, decyl methacrylate, iso-decyl methacrylate, lauryl methacrylate, stearyl methacrylate, hydroxyethyl methacrylate, hydroxypropyl methacrylate, acetoxyethyl methacrylate, acetoxypropyl methacrylate, tert-butylaminoethyl methacrylate, 2-(3-oxazolidinyl)ethyl methacrylate, iso-bornyl methacrylate, acrylonitrile, methacrylonitrile, acrylamide and methacrylamide, allylacetoacetates, ethylene, propylene, styrene and substituted styrenes, butadiene, vinyl acetate, vinyl versatate, vinyl butyrates and other vinyl esters, halogenated vinyl monomers (e.g., vinyl chloride, vinylidene chloride, and the like), and combinations thereof. In a preferred embodiment, the monomer contains a vinylic olefin group. In another preferred embodiment, the monomer may or may not be conjugated (for example, as in butadiene or methyl methacrylate).

When used in combinations, the monomers can be combined in any amounts. Using a single monomer produces a homopolymer; while using two monomers produces a copolymer. Copolymers and homopolymers can be both referred to as "(co)polymers," and the processes by which copolymers and homopolymers are made can be referred to as "(co)polymerization."

The amount of the one or more monomers present in the emulsion polymerization mixture can be about 10 wt. % to about 60 wt. %, alternatively, about 20 wt. % to about 50 wt. % based on a total weight of the emulsion polymerization mixture.

In an alternative embodiment, the emulsion polymerization mixture can comprise one or more oligomers or oligomeric compounds, or alternatively, one or more prepolymers.

Embodiments of the one or more surfactants suitable for use in the emulsion polymerization mixture and polymerization processes discloses herein include anionic surfactants and/or non-ionic surfactants, for example, alkyl, aryl, or alkylaryl sulfates; sulfonates or phosphates of alkali metals, or the corresponding ammonium salts. Suitable surfactants also can include alkylsulfonic acids, sulfosuccinate salts, fatty acid salts, ethoxylated alcohols, amphiphilic copolymers, and combinations thereof.

The amount of the one or more surfactants present in the emulsion polymerization mixture can be about 0.05 wt. % to about 10 wt. % based on a total weight of the emulsion polymerization mixture.

Embodiments of the one or more polymerization initiators suitable for use in the emulsion polymerization mixture and polymerization processes discloses herein include one or more oxidizing agents, one or more reducing agents, or one or more of both oxidizing agents and reducing agents for oxidation-reduction reactions.

Nonlimiting examples of oxidizing agents include hydrogen peroxide, sodium peroxide, potassium peroxide, tert-butyl hydroperoxide, and tert-alkyl hydroperoxides, tert-alkyl peroxides, tert-alkyl peresters, cumene hydroperoxide, ammonium or alkali metal persulfates, alkali metal perborates (e.g., sodium perborate), perphosphoric acid and salts thereof, potassium permanganate, ammonium or alkali metal salts of peroxydisulfuric acids, and combinations thereof.

Nonlimiting examples reducing agents include ascorbic acid, iso-ascorbic acid, sodium formaldehyde sulfoxylate, sodium sulfite, sodium bisulfite, sodium thiosulfate, sodium hydrosulfite, sodium sulfide, sodium hydrosulfide or dithiosulfate, formamidinesulfonic acid, hydroxymethanesulfonic acid, sodium 2-hydroxy-2-sulfinatoacetate, acetone bisulfite, ethanolamine, glycolic acid, lactic acid, glyceric acid, malic acid and tartaric acid, and combinations thereof.

The one or more polymerization initiator can be present in an amount of about 0.001 wt. % to about 1 wt. % based on a total weight of the emulsion polymerization mixture.

Oxidation-reduction reactions of the one or more initiators can be catalyzed by metal salts such as salts of iron, copper, manganese, silver, platinum, vanadium, nickel, chromium, palladium, or cobalt. The metal salt(s) can be present in an amount of about 0.01 ppm to about 25 ppm based on a total weight of the emulsion polymerization mixture.

The water suitable for use in the emulsion polymerization mixture and polymerization processes discloses herein can be obtained from any source. The amount of water can be the remaining weight which, in addition to the other components of the emulsion polymerization mixture, is sufficient to reach 100% of the desired amount (e.g., desired weight, desired volume) of the emulsion polymerization mixture.

The chain transfer compositions disclosed herein can be used alone or in combination with other suitable (second) chain transfer agents in an emulsion polymerization mixture. Thus, any of the emulsion polymerization mixtures disclosed herein can further include a second chain transfer agent, non-limiting examples of which can include n-dodecyl mercaptan, tert-dodecyl mercaptan, other chain transfer agents known in the art with the aid of this disclosure, and combinations thereof.

In an embodiment, the emulsion polymerization mixture is generally capable of free-radical polymerization to yield one or more (co)polymers. For the mixture to be capable of free radical polymerization, at least one of the components of the mixture is capable free-radical polymerization. In a particular embodiment, the polymerization initiator(s) is a free radical, defined as a compound which itself is a free radical in the mixture, is capable of becoming or transforming into a free radical in the mixture, or is capable of transforming another component into a free radical in the mixture, for example, via thermal, photochemical, electrochemical, oxidation-reduction reaction, or any other method known to those skilled in the art with the aid of this disclosure.

Also provided herein are emulsion polymerization processes for (co)polymerization of one or more monomers to produce polymers.

Embodiments of the emulsion polymerization processes include introducing a chain transfer agent composition as described herein into an emulsion polymerization mixture. The process can also include forming the emulsion polymerization mixture, and recovering a polymer from the emulsion polymerization mixture.

In forming the emulsion polymerization mixture, components (e.g., monomer, surfactant, polymerization initiator, water, or combinations thereof) of the emulsion polymerization mixture are mixed with one another. The components of the emulsion polymerization mixture can be mixed in any order. Moreover, mixing of any of the components can occur in a batch method, either at the beginning of the process, one or more times during the process, or continuously through at least a portion of the process.

In introducing the chain transfer agent composition, the disclosed chain transfer agent composition can be introduced to the emulsion polymerization mixture before, after, or during the mixing of any one or more of the components of the emulsion polymerization mixture. For example, the chain transfer agent composition can be introduced to any of the monomer, water, surfactant, and initiator before the addition of said component to the emulsion polymerization mixture containing any other component. Alternatively, the chain transfer agent composition can be introduced to the emulsion polymerization mixture after mixing monomer, water, and surfactant (in any order) and before addition of the initiator. Alternatively, the chain transfer agent composition can be introduced to the emulsion polymerization mixture after mixing all components of the emulsion polymerization mixture. Regardless of the timing of introducing the chain transfer agent composition to the emulsion polymerization mixture relative to the addition of any component of the mixture, the chain transfer agent composition can be introduced in a batch method, either at the beginning of the process, one or more times during the process, or continuously through at least a portion of the process.

The (co)polymerization reactions can have an initiation phase which can be carried out thermally, photochemically, electrochemically, by oxidation-reduction reaction, or any other method known to those skilled in the art with the aid of this disclosure. Thermal initiation can occur at a temperature of about 50° C. to about 100° C.

The polymer resulting from the polymerization reactions which occur in the emulsion polymerization mixture can be recovered by any technique known in the art with the aid of this disclosure, e.g., distillation, filtration, evaporation, flashing, other separation, or combinations thereof.

The processes for emulsion (co)polymerization as described herein can be carried out at any temperature and any pressure known to those skilled in the art with the aid of this disclosure. For example, the (co)polymerization processes can be carried out at atmospheric pressure at a temperature of about 0° C. to about 100° C., alternatively, about 10° C. to about 90° C.

Examples

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Production of $C_{10}$ Mercaptans

Hydrogen sulfide ($H_2S$) and a feedstock comprising branched $C_{10}$ monoolefins were reacted in the presence of various initiating agents: UV radiation, an acid catalyst, and a hydrodesulfurization (HDS) catalyst.

Various feedstocks (e.g., olefin feedstocks) were used for reacting with $H_2S$ to produce mercaptans and/or sulfides. More specifically, $C_{10}$ monoolefin feedstocks obtained from 1-hexene production processes were used as feedstocks for reacting with $H_2S$ to produce mercaptans.

Gas chromatography (GC)-mass spectrometry (MS) (GC-MS) and nuclear magnetic resonance (NMR) spectroscopy were used for analyzing the composition of olefin feedstocks obtained from 1-hexene production processes as well as the products of the reaction of the olefin feedstocks with $H_2S$.

The compositions comprising $C_{10}$ monoolefins were analyzed by gas chromatography-mass spectrometry (GC-MS) using a 15 m×0.25 mm×0.5 μm DB-5 column and/or a 40 m×0.1 mm×0.1 μm DB-1 column to determine component identities, and standard gas chromatography (GC) using a 60 m×0.32 mm×1 μm DB-1 column to determine the quantity of the components present in the compositions. These compositions are measured in area %, which is substantially similar and analogous to wt. %.

Table 1 provides representative information about the typical composition of such an olefin feedstock obtained from 1-hexene production processes to react with $H_2S$ to produce mercaptans.

TABLE 1

Composition of Mixed Decene Olefin Feedstock

| Chemical | GC Area % | | Normalized % |  |
|---|---|---|---|---|
| Cyclohexane | 2.148 | | | |
| Octane | 0.036 | $C_8$ olefins | 1.17 | 1.24 |
| 1-octene | 1.135 | | | |
| Octane | 0.146 | octane | 0.15 | 0.16 |
| Ethylbenzene | 1.684 | | | |
| 3-propyl-1-heptene | 14.590 | $C_{10}$ olefins | 84.16 | 89.11 |
| Decene | 0.164 | | | |
| 4-ethyl-1-octene | 13.134 | | | |
| 5-methyl-1-nonene | 32.144 | | | |
| Decene | 0.647 | | | |
| 2-butyl-1-hexene | 9.960 | | | |
| Decene | 0.320 | | | |
| 4/5 decene | 9.116 | | | |
| 1-decene | 4.086 | | | |
| Decene | 0.360 | decane | 0.36 | 0.38 |
| 2-ethyl-1-hexanol | 1.379 | | | |
| dodecene isomers | 0.448 | $C_{12}$ olefins | 1.29 | 1.37 |
| 1-dodecene | 0.842 | | | |
| Dodecane | 0.182 | dodecane | 0.18 | 0.19 |
| Tetradecenes | 6.710 | $C_{14}$ olefins | 6.71 | 7.11 |
| Tetradecane | 0.198 | tetradecane | 0.2 | 0.21 |
| Octadecene | 0.222 | $C_{18}$ olefins | 0.22 | 0.23 |
| 2-ethylhexyl-2-ethylhexanoate | 0.069 | | | |
| Unknowns | 0.281 | | | |
| Total | 100.000 | total olefins | 94.44 | 99.06 |

Normalized to include only octane, decane, dodecane, tetradecane, and $C_8$, $C_{10}$, $C_{12}$, $C_{10}$, and $C_{18}$ olefins As can be seen from Table 1, the total olefin content of this particular olefin feedstock (excluding the compounds that are not products of the 1-hexene process) sample is 94.44 area %, and 84.16 area % of the total feedstock is $C_{10}$ olefin isomers. The $C_{10}$ olefins represent over 89 area % of the total olefin content when the sample is normalized to remove the compounds that are not products of the 1-hexene process. Cyclohexane, ethylbenzene, and 2-ethylhexanol can be present in the olefin feedstock as residual components of the 1-hexene oligomerization process. The structures of $C_{10}$ isomers that can be present in the olefin feedstock are shown in Table 2.

TABLE 2

Structures of Mixed Decene Olefins and Mercaptan Reaction Products

| Decene fraction | Olefin | Major UV Product | Major Acid Catalyst Product |
|---|---|---|---|
| 5-methyl-1-nonene 32.14% (38.19) | | SH | SH |

TABLE 2-continued

Structures of Mixed Decene Olefins and Mercaptan Reaction Products

| Decene fraction | Olefin | Major UV Product | Major Acid Catalyst Product |
|---|---|---|---|
| 3-propyl-1-heptene 14.59% (17.33) | (structure) | (structure with SH) | (structure with SH) |
| 4-ethyl-1-octene 13.13% (15.60) | (structure) | (structure with SH) | (structure with SH) |
| 2-butyl-1-hexene 9.96% (11.83) | (structure) | (structure with SH) | (structure with HS) |
| 4/5 decene 9.12% (10.83) | (two structures) | (two structures with SH) | (two structures with SH) |
| 1-decene 4.09% (4.86) | (structure) | (structure with SH) | (structure with SH) |

In Table 2, the first column provides the name of the isomer, the GC area % of that component in the feedstock from Table 1, and the normalized amount of the isomer typically found in just the $C_{10}$ fraction of the feedstock. Table 2 also displays the structure of the mercaptans that are produced from the $C_{10}$ olefin isomers. The second column shows the structure of the major $C_{10}$ olefin isomers in the feedstock; the third column displays the structure of the major mercaptan isomers produced by a UV-initiated reaction with $H_2S$; and the fourth column displays the structure of the major mercaptan isomers produced by acid catalysis.

A sample of the olefin feedstock was fractionated (e.g., distilled) and only the $C_{10}$ fraction was isolated in high purity (e.g., a purified feedstock). This product was submitted for $H^1$ and $C^{13}$ NMR. The NMR analysis (in mol %) was consistent with the information provided by GC-MS. The NMR confirmed that about 11 mol % of the total was vinylidene (2 butyl-1-hexene isomer) and about 11 mol % of the total purified feedstock was internal olefins (linear decene isomers). The nomenclature for the various $C_{10}$ isomer products is shown in Table 3.

TABLE 3

Nomenclature for Mercaptan Reaction Products

| $C_{10}$ Olefin | UV-initiated Mercaptans | Acid-catalyzed Mercaptans |
|---|---|---|
| 5-methyl-1-nonene | 5-methyl-1-mercapto-nonane | 5-methyl-2-mercapto-nonane |

TABLE 3-continued

Nomenclature for Mercaptan Reaction Products

| $C_{10}$ Olefin | UV-initiated Mercaptans | Acid-catalyzed Mercaptans |
|---|---|---|
| 3-propyl-1-heptene | 3-propyl-1-mercapto-heptane | 3-propyl-2-mercapto-heptane |
| 4-ethyl-1-octene | 4-ethyl-1-mercapto-octane | 4-ethyl-mercapto-octane |
| 2-butyl-1-hexene | 2-butyl-1-mercapto-hexane | 5-mercapto-5-methyl-nonane |
| 4-decene | 4-mercapto-decane 5-mercapto-decane | 4-mercapto-decane 5-mercapto-decane |
| 5-decene | 4-mercapto-decane 5-mercapto-decane | 4-mercapto-decane 5-mercapto-decane |
| 1-decene | 1-mercapto-decane | 2-mercapto-decane |

Reaction of $H_2S$ with the olefin feedstock (e.g., a feedstock comprising branched $C_{10}$ monoolefins) by UV initiation (e.g., using UV radiation) yielded mostly primary mercaptans, since the terminal olefin and vinylidene isomers yield predominately the anti-Markovnikov product. The minor components were the secondary mercaptans from the terminal olefin and a tertiary mercaptan from the vinylidene isomer. Typically, UV-initiation of a terminal olefin produced primary mercaptans in 92-96 area % range and secondary mercaptans in 4-8 area % range. The linear internal olefin isomers present in the feedstock primarily produced secondary mercaptan isomers. Thus, for the composition of the feedstock disclosed herein, the distribution of mercaptans (i.e., the distribution within the $C_{10}$ fraction) in the resulting reaction product was predominately primary mercaptans at about 80-90 area %. Secondary mercaptans were present at 10-20 area %, and tertiary mercaptans were present at about 0-3 area %. These ranges were calculated by NMR analysis of the reaction product.

Reaction of $H_2S$ with the olefin feedstock over an acid catalyst (such as Filtrol® 24 or Filtrol® 24X), produced as the major product the Markovnikov product. Thus, the major mercaptan isomers contained secondary mercaptans with some tertiary mercaptan. The relative ratio of mercaptans was estimated at 85-90% secondary mercaptan and 10-15% tertiary mercaptan.

Reaction of $H_2S$ with a feedstock comprising branched $C_{10}$ monoolefins in the presence of a hydrodesulfurization (HDS) catalyst (such as Haldor Topsoe TK-554 or TK-570) produced mercaptans primarily similar in distribution to those produced by acid catalysis, which is the Markovnikov distribution. However, the HDS catalyst also produces a significant amount of the anti-Markovnikov product depending on the conditions used in the reaction step. Thus, under the conditions evaluated for this disclosure, the product produced by the HDS catalyst was a blend of the product produced via acid catalysis with some of the components produced by the UV-initiated reaction.

As will be appreciated by one of skill in the art, and with the help of this disclosure, the actual composition of the reaction product will ultimately depend on a number of factors: the exact composition of the feedstock, the ratio of $H_2S$ to olefin that is used to produce the thiols, the catalytic method used to react the $H_2S$ and olefin (UV vs. acid catalysis vs. HDS catalysis) to produce the product, etc. The final product (e.g., any cuts separated from the crude to form, for example, a commercial product) will also depend on the purification step to remove lights and whether a final product containing both mercaptan and sulfide fractions is desired or just one of the fractions, e.g., a mercaptan fraction or a sulfide fraction, is desired.

$H_2S$ to Olefin Ratio:

The $H_2S$ to olefin molar ratio is an important parameter in determining the amount of mercaptan and sulfide produced during the reaction step. This can be true regardless of the catalytic method employed. Without wishing to be limited by theory and in general, the higher the $H_2S$ to olefin molar ratio, the greater the amount of mercaptans that will be produced compared to the amount of sulfides produced.

A general reaction scheme for addition of $H_2S$ to an olefin is shown in FIG. 1, regardless of catalytic method. For a $C_{10}$ olefin fraction, R, R' and R" can be H or $C_1$-$C_8$ with the total of R+R'+R"=8. For 1-decene, R and R'=H and R"=8 and can be a linear or branched alkyl group. For the major isomers in a $C_{10}$ olefin fraction (e.g., a second feedstock as disclosed herein), 5-methyl-1-nonene: R and R'=H and R"=8, but the alkyl group contains branching at the $3^{rd}$ carbon atom of the $C_8$ fraction.

A sulfide fraction can be produced by further reaction of a mercaptan isomer with an olefin. The generic structures of such sulfides are shown in FIG. 1 and this fraction will consist of a variety of isomers with several possible combinations of sulfide structures depending on whether the sulfide is primary to primary, primary to secondary, primary to tertiary, secondary to secondary, secondary to tertiary, or tertiary to tertiary. The structures are complicated by the fact that on the two portions of the sulfide the R, R' and R" value can be the same or different depending on which mercaptan isomer reacts with which olefin isomer. The total number of carbon atoms of the two portions of the sulfide can also have different values for R+R'+R", although the most dominant combination will be where both sides each have a sum of 8 since the $C_{10}$ fraction predominates in the first feedstock and in the second feedstock.

Mercaptan Preparation Procedure:

The tertiary dodecyl mercaptan (TDDM) used for this work were commercial product samples obtained from the Chevron Phillips facility in Borger, Tex. The mixed $C_{10}$ mercaptan compositions were prepared using the following procedures.

Reaction Conditions:

Three different reaction methods were used to perform the reaction of $H_2S$ with a feedstock comprising branched $C_{10}$ monoolefins: UV initiation, acid catalysis, and HDS catalysis.

$H_2S$ Removal: In laboratory experimentation, $H_2S$ was removed using a rotovapor apparatus under conditions of reduced pressure. Under these conditions, $H_2S$ was removed without removing significant quantities of light compounds.

Analytical Methods:

The weight percentage of thiol (mercaptan) sulfur (wt. % SH) was determined analytically by titration using iodine in water as the titrant and methylene chloride/isopropanol as the solvent system. Such titration can also be done by using a silver nitrate titration method. Total sulfur was measured by X-ray using a model SLFA-20 Horiba sulfur-in-oil analyzer. GC analysis was performed using an Agilent Technologies 7890A GC with a flame ionization detector. A 2 m×0.25 mm×1.0 μm film DB-1 capillary column was used for the separation. Operating conditions were as follows: 70° C. initial temperature, 2 min hold time, 8° C./min ramp rate to 200° C. and then 15° C./min ramp rate to 300° C. and hold for 10 minutes. A 2 ml/min helium flow rate at constant flow conditions was used. The injector temperature was set at 275° C. and the detector temperature at 300° C. As described previously, these data from these compositions were reported in area %, which is substantially similar and analogous to wt. %. Olefin conversion was monitored using Raman spectroscopy, with a Kaiser Optical System RXN2 4-channel spectrometer. The peak centered at 1640 cm$^{-1}$ was the vinyl olefin, while the peak centered at about 1670 cm$^{-1}$ was the internal olefin.

Figure 2:
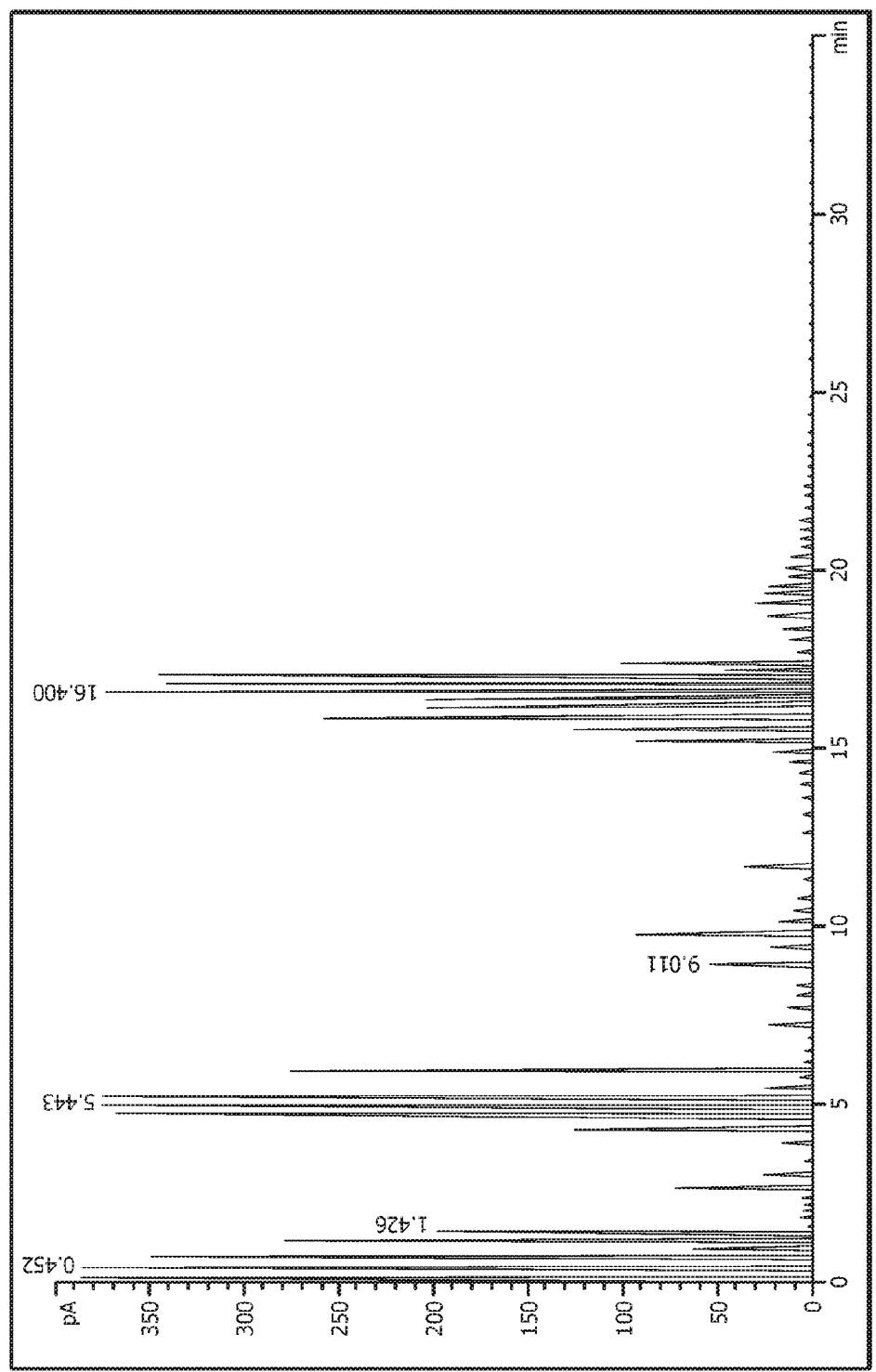
FIG. 2 displays a GC trace of a crude product from an UV initiated reaction after removal of residual $H_2S$.
Figure 4:
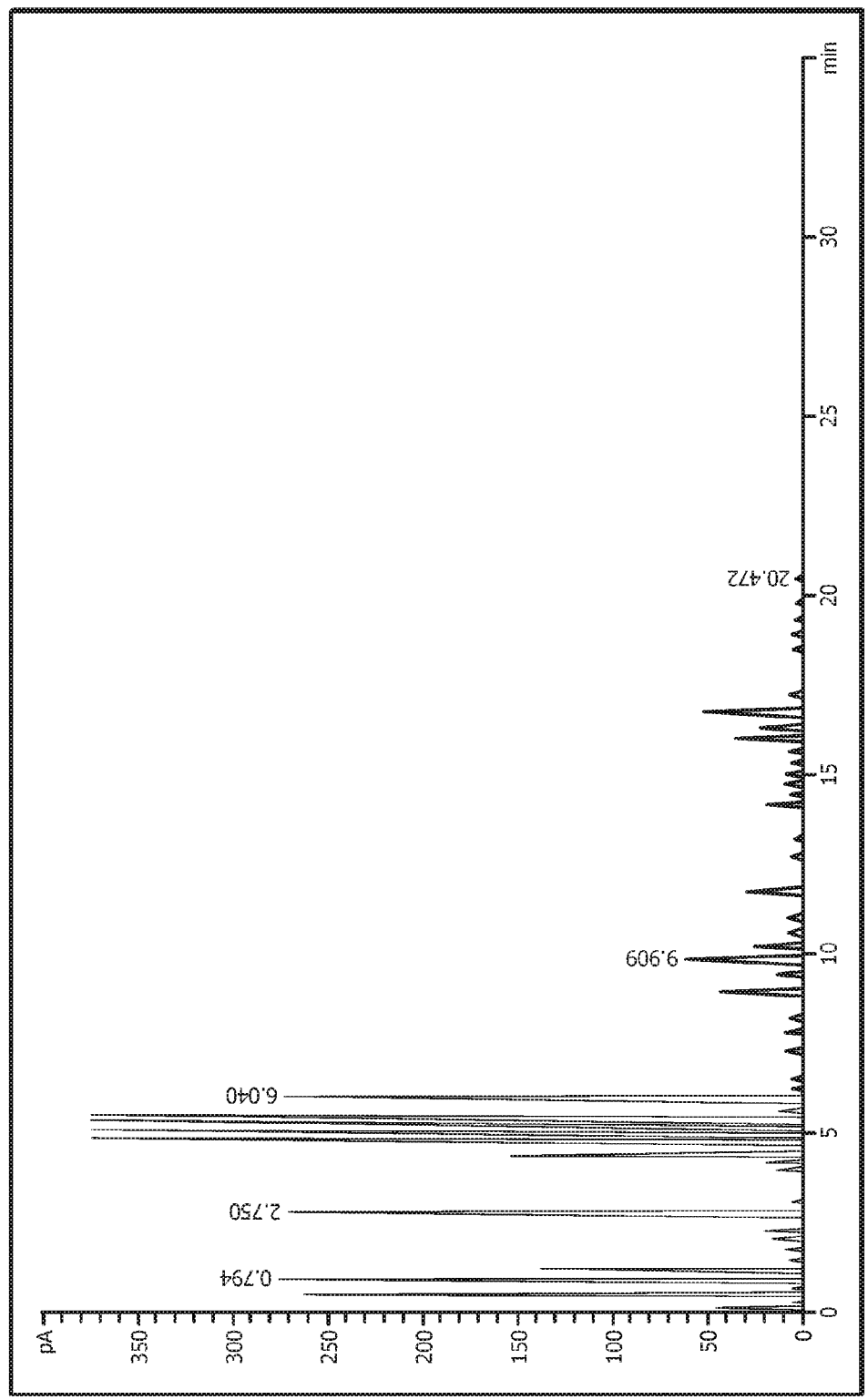
FIG. 4 displays a GC trace of a crude product from an UV initiated reaction after removal of residual $H_2S$.

UV Initiation:

Reactions were performed using either a 1.5 L or a 5-liter UV reactor equipped with a 100 watt lamp and ballast. The two reactors are substantially the same configuration, and the only difference in operation is the amount of reactants added to the reactor. The reaction mixture was stirred at 500-1,000 RPM. The reaction temperature was controlled with a bath set at 25° C., but the heat of reaction did reach about 40° C. The lamp operated at 1.1-1.5 amps and 28-103 volts over the course of the reaction, operating at lower amps and higher voltage as it warmed up. The reaction pressure was 220-280 psig (1,516 kPag-1,930 kPag) during the actual reaction time. The $H_2S$:olefin molar ratios were varied from 1.0 to 10.2; however, in theory, any $H_2S$ to olefin ratio could be used. The reaction was completed in about 30 minutes based on the results of Raman Spectroscopy but was allowed to continue for 60 minutes to ensure completion. The main isomers from this reaction are listed in Table 3. FIGS. 2 and 4 show typical gas chromatogram results of the crude reaction product resulting from the UV-initiated process after the removal of $H_2S$.

The relative amounts of $C_{10}$ mercaptan isomers, intermediate mercaptans and sulfide heavies depended on the ratio of $H_2S$ to olefin feedstock during the reaction step. Conventional wisdom would suggest that the $C_{10}$ mercaptan fraction would have too strong of an odor to be acceptable for certain applications, and that the sulfide fraction might have a better odor. Surprisingly and unexpectedly, after removing these samples from the reactor and venting off the residual $H_2S$ using a rotoevaporator, the odor of this crude product was good. The limited odor of these compositions was an unexpected result that makes these compositions advantageous for use as chain transfer agents.

Figure 3:
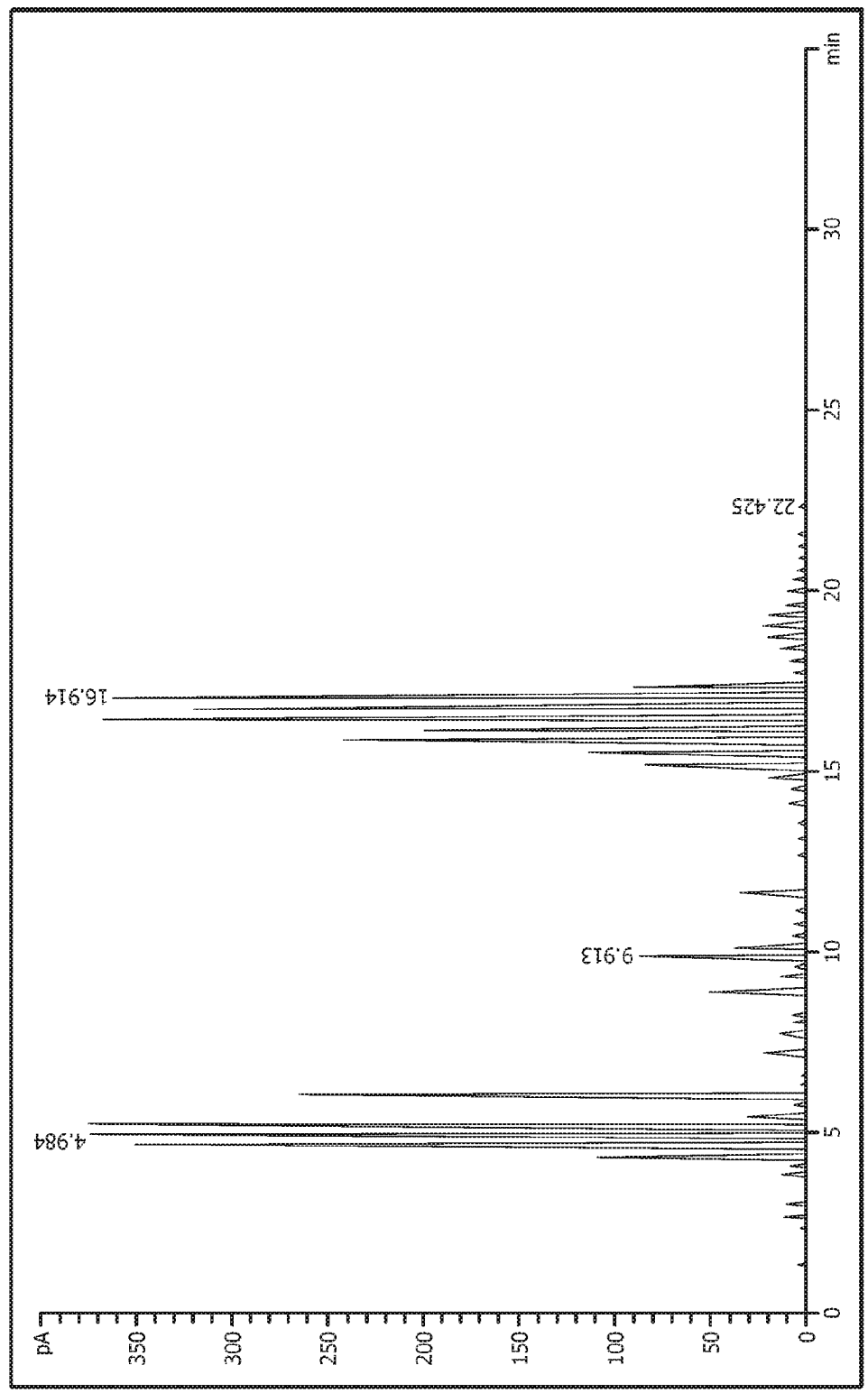
FIG. 3 displays a GC trace of a reaction product from an UV initiated reaction after removal of lights.
Figure 5:
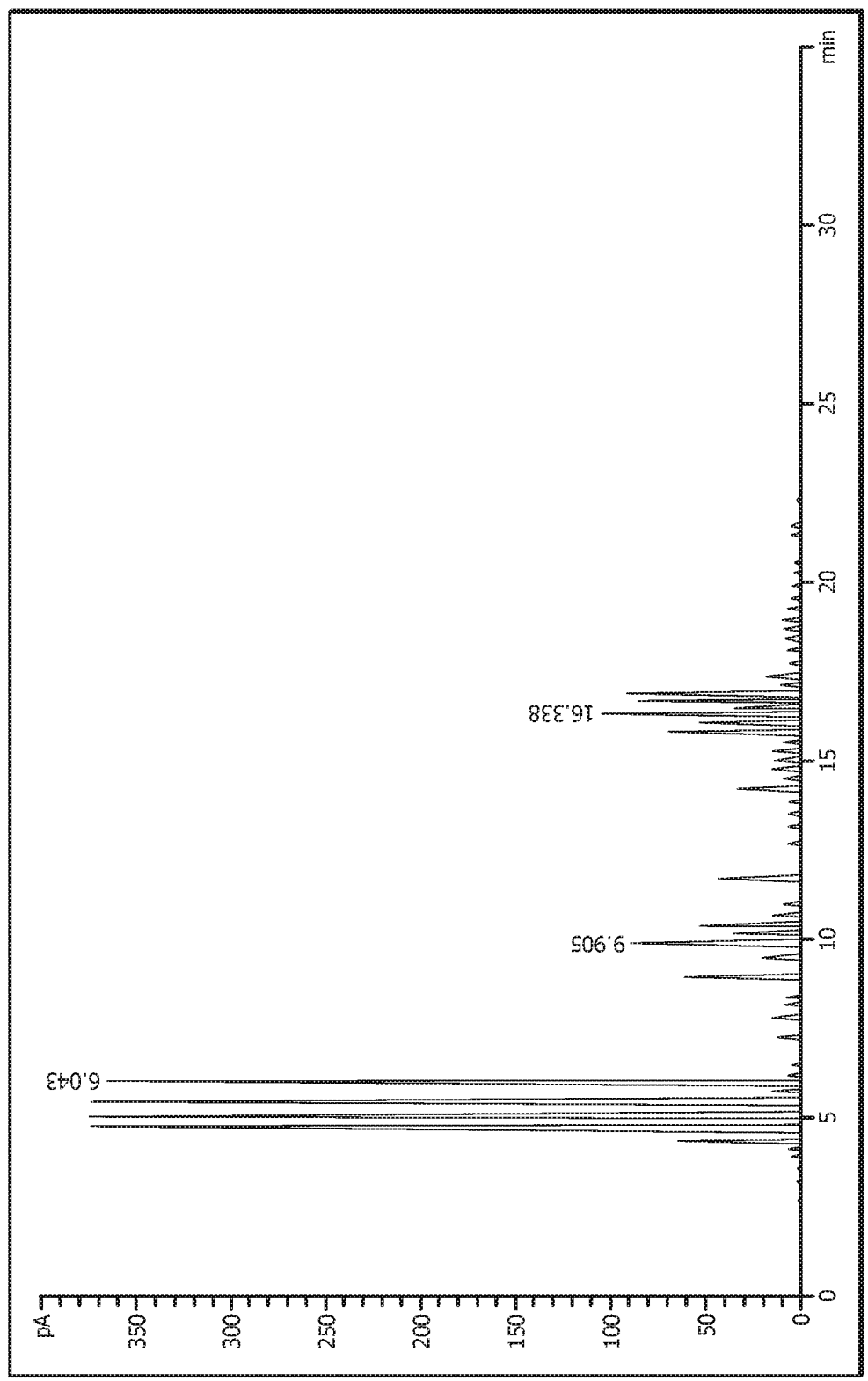
FIG. 5 displays a GC trace of a reaction product from an UV initiated reaction after removal of lights.

The composition of the UV-produced product can be described in broad terms as follows, and taking into account that the crude reaction product can be subsequently separated into different fractions of different compositions and purity. In broad terms, the product consists of three general fractions as produced from the kettle product after removal of the unwanted lights fraction. FIGS. 3 and 5 show gas chromatogram results of the reaction product resulting from the UV-initiated process following removal of the light fraction. The $C_{10}$ mercaptan fraction comprised from 50-100 wt. % of the crude kettle composition. The mercaptan functionality of the $C_{10}$ mercaptan fraction was 80-90% primary mercaptan, 5-18% secondary mercaptan and 0-3% tertiary mercaptan. This was the fraction that eluted in the 3.8-6.5 minute range under the GC conditions used. The intermediate fraction, which eluted in the 6.5-14 minute region, was predominately mercaptan isomers in the $C_{12}$ to $C_{18}$ range with a distribution of functionality that can be similar to that for the $C_{10}$ isomer fraction. The intermediate fraction comprised from 0 to 12 area % of the kettle product. The heavy fraction (>14 minute retention time) consisted essentially of sulfides, primarily of formula $C_{10}H_{21}$—S—$C_{10}H_{21}$ isomers, as well as sulfides from $C_{12}$, $C_{14}$, $C_{16}$ or $C_{18}$ olefins and mercaptans or the asymmetric sulfides produced from the various combinations. These sulfide components comprised from 0-70 area % of the composition of the crude product.

Acid Catalysis:

Acid catalyzed reactions produced a different distribution of isomer products than obtained by UV-initiation reaction of $H_2S$ and the olefin feedstock comprising branched $C_{10}$ monoolefins.

Figure 6:
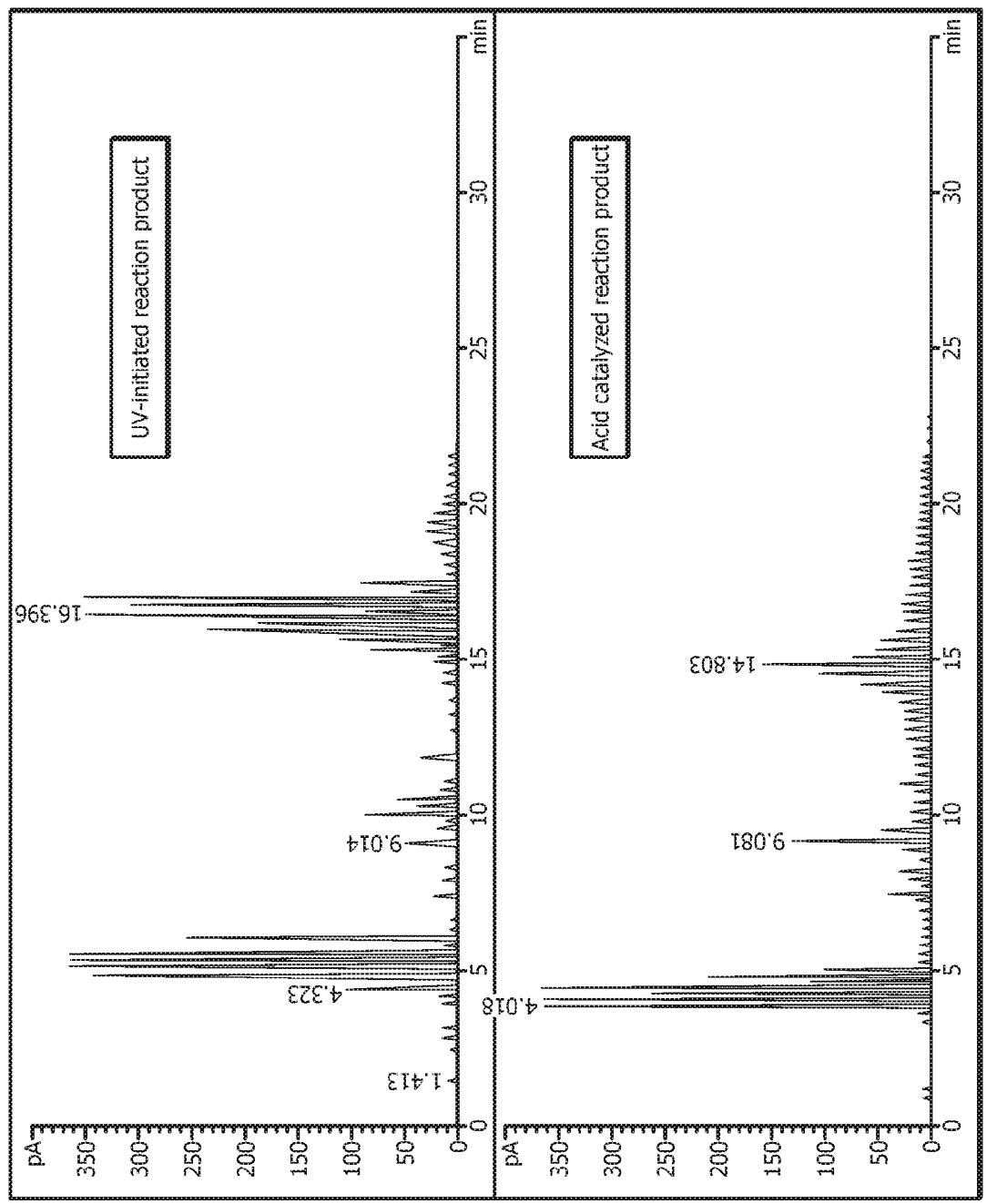
FIG. 6 displays a comparison of GC traces for a product obtained by UV initiation and a product obtained by acid catalysis, and particularly, representative GC profiles of the crude $C_{10}$ mercaptan/$C_{20}$ sulfide reaction product after removal of the light fraction. The upper chromatogram is the UV-initiated $C_{10}$ mercaptan product, and the lower chromatogram is the acid catalyzed $C_{10}$ mercaptan product.

The product produced via the acid catalyzed addition of $H_2S$ to the feedstock comprising branched $C_{10}$ monoolefins was prepared in a continuous flow reactor over Filtrol® 24 acid catalyst. The reactor contained 43.22 g of catalyst and the WHSV (weight hourly space velocity) was maintained at 1.0 grams of olefin per gram of catalyst per hour. The $H_2S$ to olefin molar ratio ranged from 10:1 to 1:1. The reaction temperature was between 120° C. to 220° C., and the reactor pressure was 450-460 psig (3,100 kPag-3,200 kPag). Optimum results, based on conversion and maximum $C_{10}$ mercaptan were in the 180-200° C. range and an $H_2S$ to olefin molar ratio of 5:1. A decrease in the $H_2S$ to olefin ratio resulted in a decrease in the $C_{10}$ mercaptan fraction and a corresponding increase in the sulfide fraction. FIG. 6 shows a typical gas chromatogram analysis for the crude reaction product resulting from the acid-catalyzed process as compared to that produced by the UV-initiated process.

Acid catalysis produced the Markovnikov product. The vinyl components of the feedstock comprising branched $C_{10}$ monoolefins produced secondary mercaptans. The internal olefin components produced secondary mercaptans, while the vinylidene components produced tertiary mercaptans. Thus, the composition of the $C_{10}$ mercaptan fraction isomers was different when compared to the composition of the product obtained by UV-initiation. For example, the 5-methyl-1-nonene isomer produced 5-methyl-2-mercapto-nonane by acid catalysis; and 5-methyl-1-mercapto-nonane was the major product produced via UV-initiation, with a minor amount of the 2-mercapto isomer as a by-product. The 2-butyl-1-hexene isomer produced 5-methyl-5-mercapto-nonane via acid catalysis; while UV-initiation produced 2-butyl-1-mercapto-hexane.

As with the product produced via UV-initiation, the product obtained by acid catalysis consisted of three general fractions produced as kettle product after removal of the unwanted lights fraction. The $C_{10}$ mercaptan fraction comprised from 50-100 wt. % of the crude kettle composition. The mercaptan functionality of the $C_{10}$ fraction was 85-95% secondary mercaptan and the remainder tertiary mercaptan. These isomers eluted in the 3.1-6.5 minute range under the utilized GC conditions.

The intermediate fraction consisted of those mercaptan peaks in the 6.5-14 minute range. However, the functionality of the mercaptans was secondary and tertiary $C_{12}$ to $C_{18}$ mercaptans. The intermediate fraction comprised 5-15% of the total kettle composition.

The sulfide fraction comprised 0-70% of the composition of the kettle product. The fraction consisted of sulfides primarily of formula $C_{10}H_{21}$—S—$C_{10}H_{21}$. However, the isomer identity was different than that for the product produced via UV-initiation. The acid produced sulfide product was based on secondary and tertiary mercaptans rather than predominately primary mercaptans as in the UV-initiated produced product.

Figure 7:
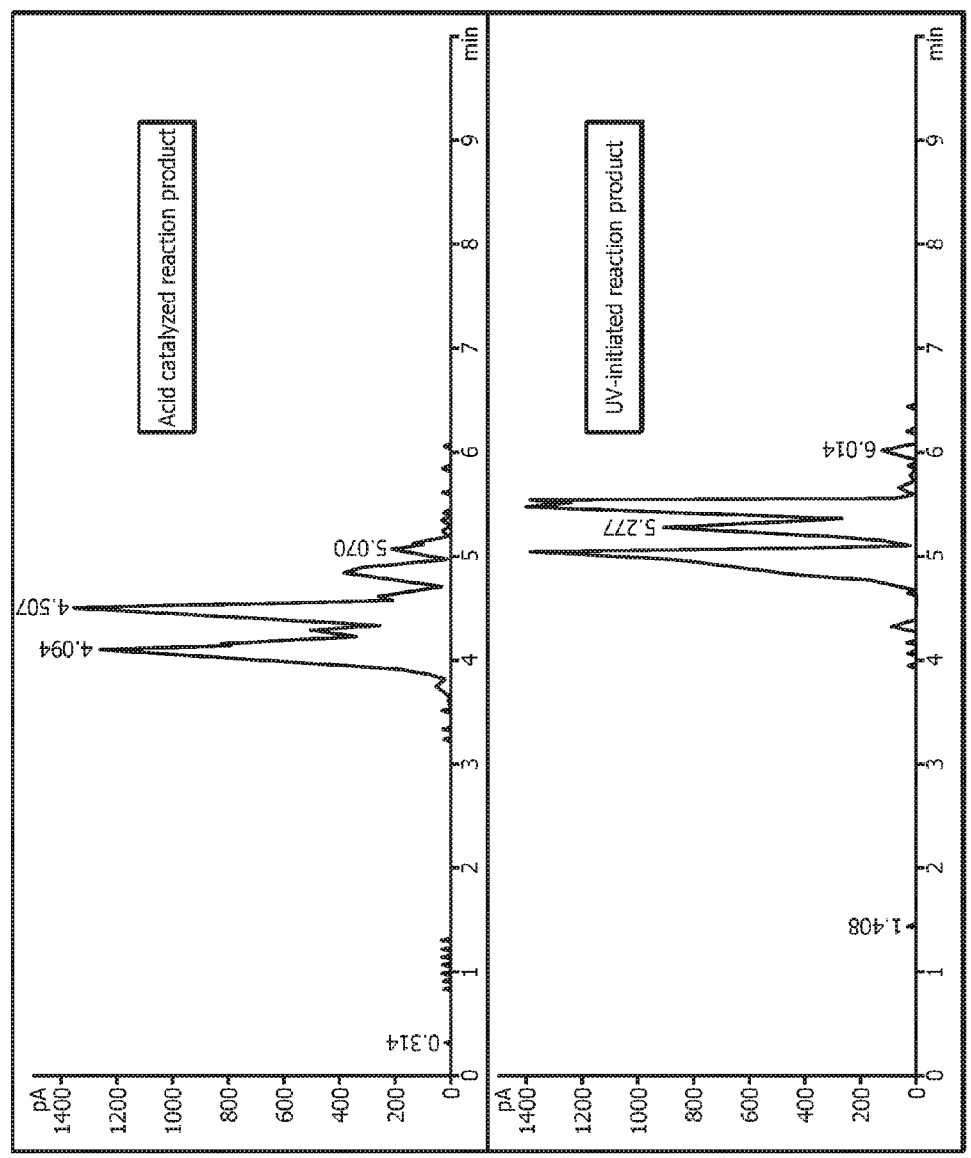
FIG. 7 displays a comparison of GC traces for a $C_{10}$ mercaptan fraction isolated from a product obtained by UV initiation and a $C_{10}$ mercaptan fraction isolated from a product obtained by acid catalysis, and particularly, representative GC profiles of the purified $C_{10}$ mercaptan reaction product. The upper chromatogram is the acid catalyzed $C_{10}$ mercaptan product, and the lower chromatogram is the UV-initiated $C_{10}$ mercaptan product.

For both the UV-initiated and acid catalyzed product, purified samples of $C_{10}$ mercaptans were prepared. The purified $C_{10}$ mercaptan samples were prepared via distillation using a 52" column packed with stainless steel packing. The first 7 fractions removed from the crude reaction product were considered to be the light fraction. This distillation step was considered to be complete when the kettle temperature increased from 100° C. to 121° C. and the head temperature increased from room temperature to 98.9° C. Cuts 8 to 13 were considered to be the intermediate fraction and included the purified $C_{10}$ mercaptans. These cuts were collected at a kettle temperature of 122° C. to 154° C. and a head temperature of 99° C. to 105° C. Cuts 8 to 11 from the UV-initiated product and cuts 5 to 11 from the acid catalyzed product were used for evaluation as chain transfer agents. Gas chromatograms representative of the typical purified $C_{10}$ mercaptan compositions (with lights, intermediates other than $C_{10}$ mercaptans, and heavies removed) from both the UV-initiated and acid catalyzed reactions are shown in FIG. 7.

HDS Catalysis:

Reactions utilizing HDS catalysis produced mercaptans that were primarily similar in distribution to those produced by acid catalysis, which is the Markovnikov distribution. However, there was a tendency to also produce some of the anti-Markovnikov distribution depending on the specific conditions utilized in the reaction step. Thus the product produced by the HDS catalyst appeared to be a blend of product produced primarily via acid catalysis with some of the components of the UV-initiated reaction.

The HDS reaction conditions were as follows: WHSV was varied from 0.75 to 2 grams of olefin per gram of catalyst per hour; the molar ratio of $H_2S$ per olefin was varied from 2:1 to 10:1; the average reaction temperature was 180° C. to 220° C. The catalyst used was cobalt molybdenum on alumina, examples being to Haldor Topsoe TK-554, TK-570, or similar. Olefin conversion, as determined by Raman Spectroscopy, was in the 88-97 mol % range.

Figure 8:
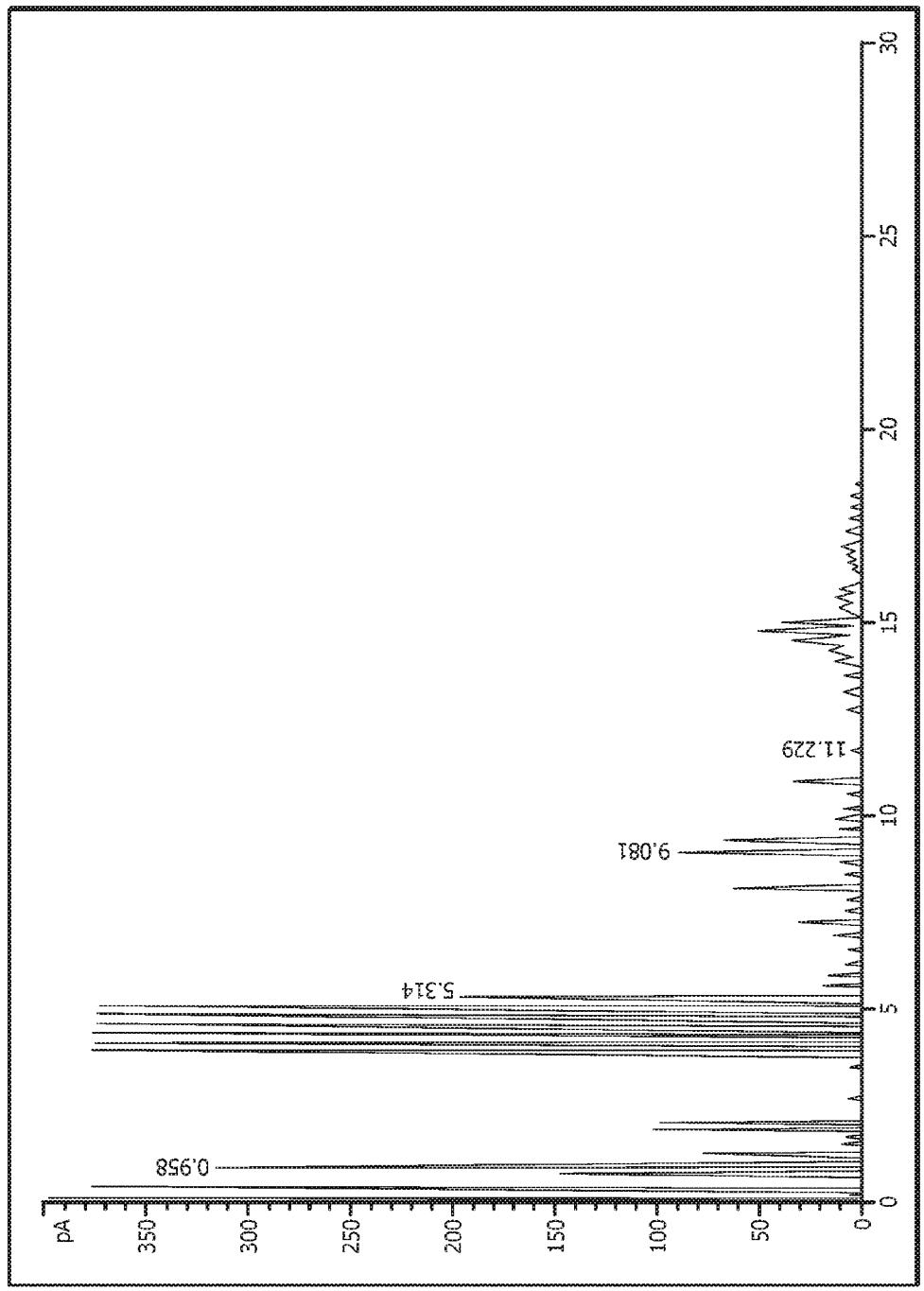
FIG. 8 displays a GC trace of a crude product from a reaction catalyzed by a hydrodesulfurization catalyst after removal of residual $H_2S$.
Figure 9:
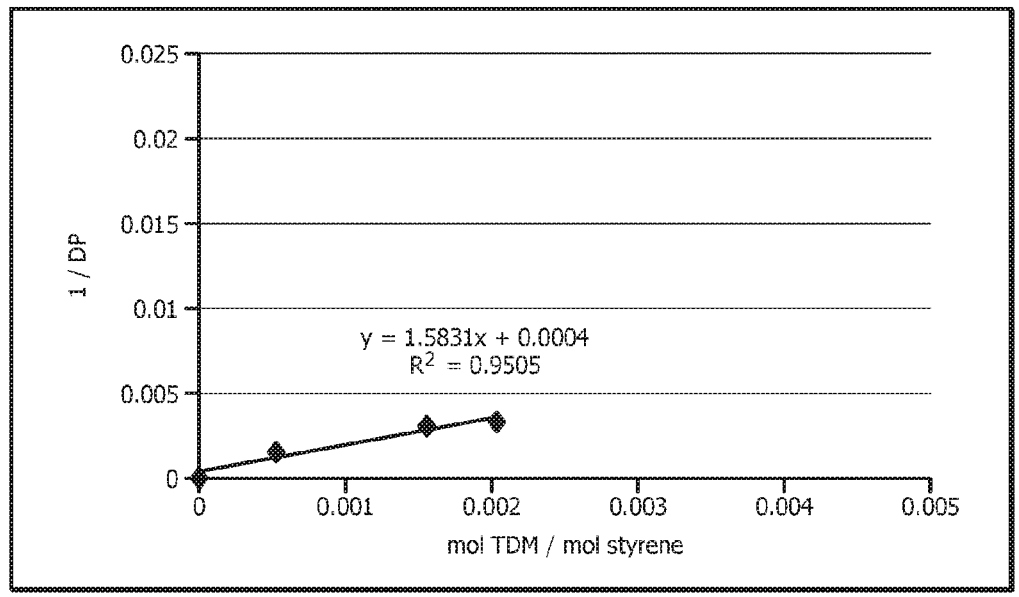
FIG. 9 shows a plot used to calculate the chain transfer constant at early conversion for TDDM (about 25 minutes post-styrene addition)
Figure 10:
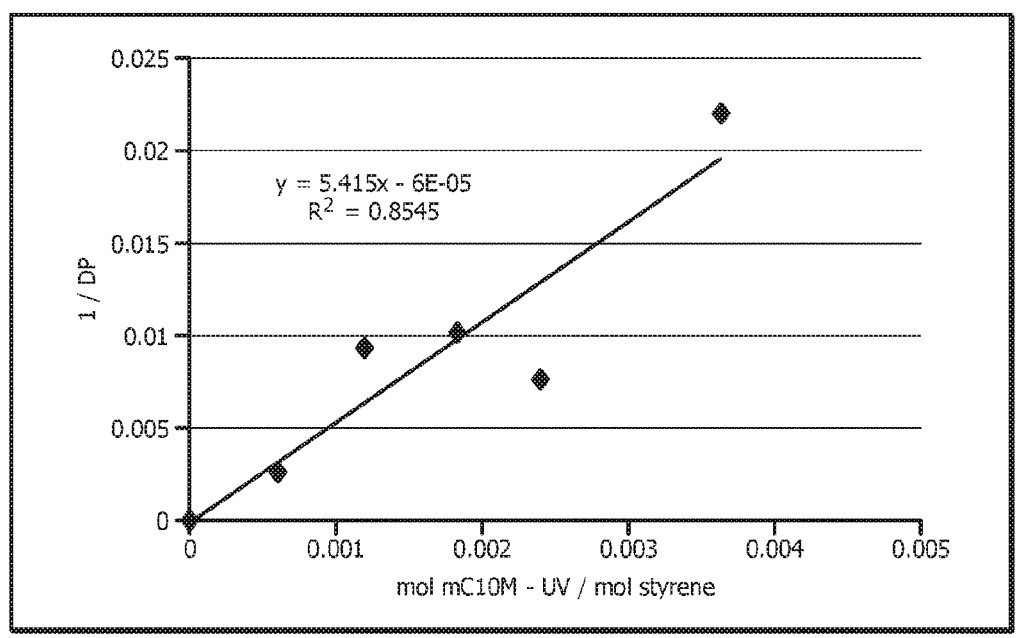
FIG. 10 shows a plot used to calculate the chain transfer constant at early conversion for mC10M-UV (about 25 minutes post-styrene addition)
Figure 11:
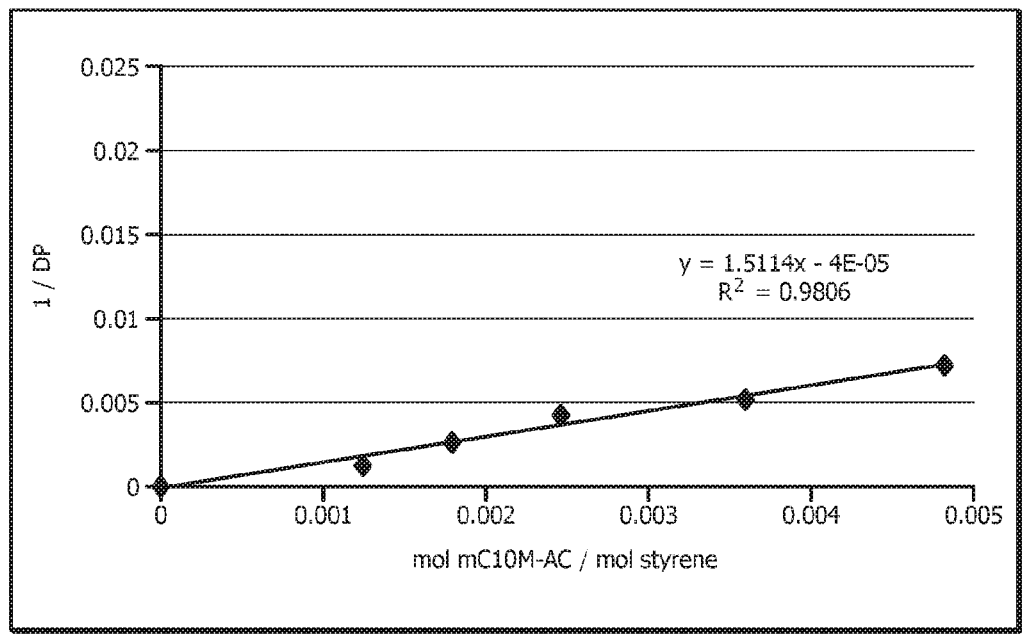
FIG. 11 shows a plot used to calculate the chain transfer constant at early conversion for mC10M-AC (about 25 minutes post-styrene addition)
Figure 12:
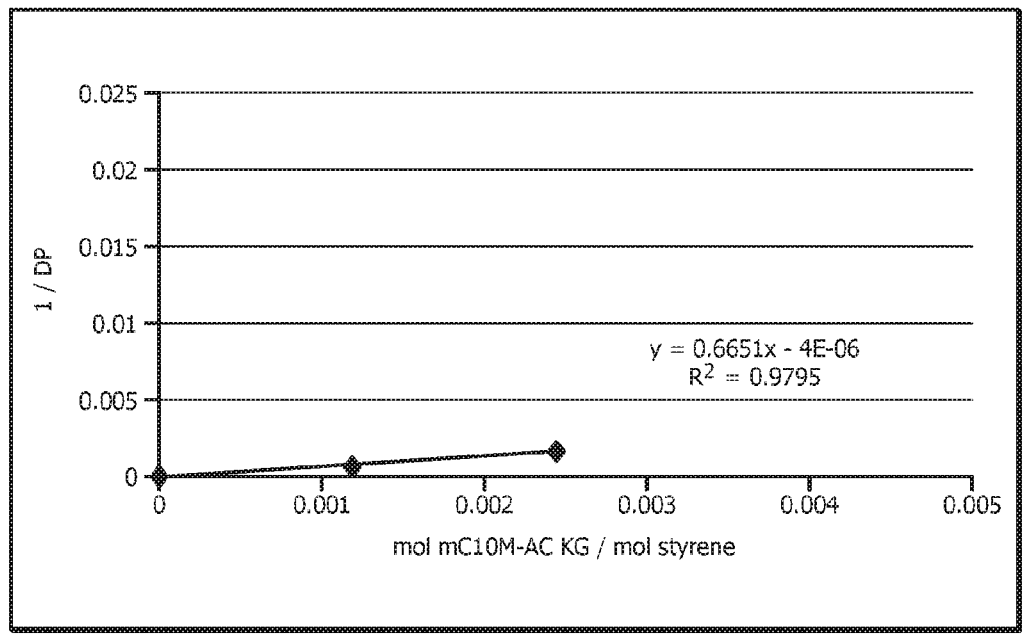
FIG. 12 shows a plot used to calculate the chain transfer constant at low conversion for mC10M-AC KG (about 25 minutes post-styrene addition).

Under similar conditions of WHSV, ratio and temperature, the HDS catalyzed reaction produced more $C_{10}$ mercaptan fraction and less sulfide fraction than the acid catalyzed reaction. Comparison of the GC analysis of the crude reaction product produced from the HDS catalyzed reaction of $H_2S$ and branched $C_{10}$ monoolefins showed that the HDS-catalyzed reaction produced a crude reaction product that was a blend of the product compositions produced by the UV-initiated and acid-catalyzed reactions. FIG. 8 shows a typical gas chromatogram analysis of the crude reaction product (with only $H_2S$ removed) resulting from the HDS catalyzed reaction.

Emulsion polymerization reactions were performed using samples of the mixed decyl mercaptan product resulting from both UV-initiated reactions and acid-catalyzed reactions. Additionally, both the crude kettle-grade reaction product (i.e., product with only the $H_2S$ removed) as well as purified reaction product (subjected to the distillation steps previously described) were evaluated.

Emulsion Polymerization Using the Disclosed Compositions

A four-necked, jacketed-reactor was fitted with an overhead mixer, reflux condenser, temperature probe, and additional funnel. To the reactor, 180 g of distilled water and 0.8 g of KOH were added and allowed to dissolve with mixing. A circulating bath attached to the jacketed reactor was used to raise the temperature of the solution to 65° C. To the warmed solution, 4.3 grams of stearic acid was added. To a bottle containing 100 grams of styrene, 0.35 grams of 2,2' azobisisobutylnitrile (AIBN) and the $C_{10}$ mercaptan composition or the $C_{10}$ mercaptan/$C_{20}$ sulfide composition being evaluated as chain transfer agents were added. Since calculating the chain transfer constant is a function of the amount of chain transfer agent that is present, the amount of mercaptan or mercaptan/sulfide mixture added was varied from 0.1 grams to 0.81 grams per 100 grams of monomer. The mixture was then shaken by hand until all of the AIBN dissolved. This solution was transferred to the additional funnel attached to the reactor. The styrene solution was slowly added to the reactor over a time period of approximately five minutes. The reaction was sampled every 20 minutes using a pipette, and approximately 3-5 mL of sample was transferred to metal weighing pans. Immediately after transfer to the weighing pans, Irganox 1010 was added to stop the reaction, and the samples were allowed to try in the hood at room temperature for at least 12 hours. Samples were then placed in a vacuum drying oven at 120° C. for 1-2 hrs.

The sample identified as mC10M-UV in Table 4 was prepared from cuts 8 to 13 (produced via the distillation procedure previously described herein). The mercaptan sulfur content of this sample was 18.2 wt. %.

The sample identified as mC10M-AC in Table 4 was prepared from cuts 5 to 11 (produced via the distillation procedure previously described herein). The total sulfur content of this sample was 18.57 wt. % and the mercaptan sulfur content was 17.51 wt. %.

The sample identified as mC10M-AC crude in Table 4 was prepared by blending a purified sample of $C_{10}$ mercaptans (cuts 5 to 11 produced via the distillation procedure previously described herein) with the remaining kettle product (cuts 12 to 13 produced via the distillation procedure previously described herein which contained the remaining intermediate fraction and the heavy fraction) at a 50:50 weight ratio. The final composition of this sample was approximately 1 wt. % lights, 50 wt. % $C_{10}$ mercaptans, 17 wt. % intermediates (excluding $C_{10}$ mercaptans), and 32 wt. % heavies. The total sulfur content of this sample was 14.52 wt. %, and the mercaptan sulfur content was 9.89 wt. %.

Gel Permeation Chromatography (GPC) Procedure

The polystyrene samples were allowed to dissolute in 1,2,4-trichlorobenzene at a concentration of 1 mg/mL at room temperature overnight. Samples were heated to 150° C. preceding injection in the autosampler compartment of the GPC. The autosampler injected 0.250 μL of solution at a flow rate of 1 mL/min into an Agilent PL220 GPC containing one 50×7.5 mm Polymer Labs guard column, and three 7.8×300 mm HMW Styragel Waters columns. Signal was collected over 45 minutes by a Polymer Char IR4 detector and molecular weight distributions of the resulting chromatograms were calculated in reference to a known high molecular weight broad standard. Insoluble percentages were calculated based on assumed 100% solubility of a narrow molecular weight polystyrene standard (NIST).

Partitioning Tests

To a 2 oz or 4 oz bottle, 18 grams of water and 10 grams of styrene were added. To this mixture, 0.5 grams of the desired mercaptan was added. The solution was mixed for 10 minutes using a shaker. A sample was collected from the styrene layer for GC analysis, and peak areas for the styrene and mercaptan were determined. GC analysis was performed using an Agilent 7890 GC with a DB-5 column (15 m×0.25 mm×0.50 μm). The temperature of the injection port was set at 250° C. and the oven temperature was 60° C. The oven temp was held at 60° C. for 5 minutes before ramping the temperature to 300° C. at a rate of 8° C. per minute and holding at 300° C. for 15 minutes. Helium flow was 1.5 mL/min. Styrene eluted at a retention time of 5 minutes; the $C_{10}$ mercaptans eluted at retention times from 12 to 20 minutes.

Evaluation of Chain Transfer Agents

TDDM was used as the commercial standard for comparative experiments. The chain transfer constant was not readily available for styrene polymerization initiated by azobisisobutylnitrile (AIBN). However, the absolute value of the chain transfer constant is of lesser importance. Rather, it was desired to compare the performance of TDDM as a commercial standard directly to the performance of the branched $C_{10}$ mercaptan composition to determine if the $C_{10}$ mercaptan composition is an acceptable substitute for TDDM as a chain transfer agent. This was accomplished by comparing the magnitude of the two chain transfer constants, as measured under the same experimental conditions.

Calculation of chain transfer constants can be made using several different types of approximations. In this case, the effects of the transfer initiator were neglected, as they are very small when AIBN is used as the initiator. The equation used is shown as Equation 1 and is an accepted method for determining $k_{tr}/k_p$, also represented as $C_s$.

$$1/\overline{X}_n = 1/\overline{X}_{n0} + C_s[S]/[M] \qquad \text{(Equation 1)}$$

In Equation 1, $\overline{X}_n$ is number average degree of polymerization, $1/\overline{X}_{n0}$ is $\overline{X}_n$ in the absence of a chain transfer agent, and S and M are the molar concentrations of chain transfer agent and monomer used. The chain transfer constants can be determined by plotting $mol_S/mol_{styrene}$ vs $1/\overline{X}_n$ at various concentrations of S and determining the slope of the line. Based on reliability of the value, the peak molecular weight ($M_p$) was used instead of the average number molecular weight ($M_n$) for the calculation of $1/\overline{X}_n$ each case.

For the data and results shown here, samples of the polymerization experiment were taken 5-7 minutes after styrene addition was complete and then again every 20 minutes. The 5-7 minute samples in most cases yielded no GPC-measurable polymer. The results shown in Table 4 are based on samples collected around 25 minutes. FIGS. 9 to 12 show the graphs that were used to calculate the chain transfer constants, as well as the $R^2$ values for each data set.

The value for TDDM calculated using the plot of $mol_s/mol_{styrene}$ vs $1/\overline{X}_n$ did not match the literature value, which is assumed to be an initial constant; however, this was not of particular concern. Examining the data, it confirms that the acid-catalyzed $C_{10}$ mercaptan composition exhibits very good performance as a chain transfer agent, comparable to that of the standard, TDDM. Surprisingly, based on the original data set, the UV-initiated $C_{10}$ mercaptan composition exhibited an even higher constant than TDDM. This led to a further review of the initial data set.

In the initial analysis, only Sample 1 (collected at approximately 5 min), Sample 5 (collected at approximately 45 min), and Sample 7 (collected at approximately 65 min) were considered. Initially, it was believed that data collected early and late in the reaction period were of interest and that data collected during mid-reaction were of less interest. In actuality, it seems that perhaps the reaction has not sufficiently progressed at 5-7 minutes, and the data collected at 15-25 minutes are more reliable. The chain transfer constants reported in Table 4 were calculated from the data set collected at 25 minutes. Results at 5 minutes were evaluated for comparison and proved to be unreliable. For samples obtained at 25 minutes, the $R^2$ value improved significantly and results indicated that polymer collection for chain transfer analysis should be done at least beyond the 5 minute mark.

As described previously, the reaction of $H_2S$ and a feedstock comprising branched $C_{10}$ monoolefins produces a crude reaction product that comprises $C_{10}$ mercaptans, wherein the $C_{10}$ mercaptans comprise branched $C_{10}$ mercaptans, and $C_{20}$ sulfides, wherein the $C_{20}$ sulfides comprised branched $C_{20}$ sulfides. Although the compounds of primary interest for evaluation as a chain transfer agent were the purified $C_{10}$ mercaptans, the crude reaction product from the acid catalyzed reaction, which comprises both $C_{10}$ mercaptans and $C_{20}$ sulfides was also evaluated as a chain transfer agent. The chain transfer constant for this crude reaction product is also reported in Table 4 as mC10M-AC crude. The crude reaction product containing both $C_{10}$ mercaptans and $C_{20}$ sulfides exhibited a much smaller chain transfer constant compared to that exhibited by the purified $C_{10}$ mercaptans.

TABLE 4

Chain transfer constants (S) for chain transfer agents (CTA)

| CTA | S |
|---|---|
| TDDM | $15831^{0.95}$ |
| mC10M-UV | $54150^{0.95}$ |
| mC10M-AC | $15114^{0.98}$ |
| mC10M-AC crude | $6030^{0.98}$ |

In Table 4, chain transfer constants (S) were calculated for the listed chain transfer agents (CTA) using Equation 1 and plotting $1/\overline{X}_n$ vs $[S]/[M]$. The $R^2$ value is reported in Table 4 as the superscript next to S.

In emulsion polymerization, how reagents partition to different phases is also of interest. Without wanting to be bound by theory, the more preference a reagent (i.e., a chain transfer agent), has for the oligomer/polymer droplet versus the water phase, the more available it is to participate in the reaction. This means that less of a reagent that prefers the organic phase is required as compared to one that partitions more equally between phases. This work was originated to investigate mixed purified mixtures of $C_{10}$ mercaptans as well as mixtures of $C_{10}$ mercaptans and $C_{20}$ sulfides and compare their performance to TDDM as the standard.

Partitioning test data and results are reported in Table 5. The percent partitioned to styrene was calculated by performing gas chromatography analysis on a sample of the styrene phase and integrating the mercaptan and styrene peaks to determine the percent mercaptan present. The ratio of % mercaptan measured by GC compared to the known weight percent of mercaptan added to the mixture gives the percent mercaptan partitioned into styrene. Results indicate that purified $C_{10}$ mercaptans have slightly less preference for styrene over water than $C_{12}$ mercaptans (i.e., TDDM). While not wanting to be bound by theory, the shorter carbon chain seems a reasonable explanation for the difference. The fact that the difference is not substantial means that amounts of $C_{10}$ mercaptan similar to the amounts of TDDM that are typically used will be effective, assuming the chain transfer constant is similar. The crude reaction product samples, which comprise a mixture of $C_{10}$ mercaptans and $C_{20}$ sulfides, showed a higher preference for the styrene phase. Since these compositions are about 10% by weight $C_{20}$ sulfides, the polarity change would suggest a strong preference for the styrene phase as observed. If sulfides are not active, they will be in the polymer droplet phase and could conceivably interfere with chain transfer. The chain transfer constant calculated from these results and reported herein supports the conclusion that the sulfides are interfering with the chain transfer reaction.

TABLE 5

Partitioning Test Results

| Description | H20, g | Styrene, g | Mercaptan added, g | % mercaptan as % of styrene | Mercaptan area %, GC | % partitioned in styrene |
|---|---|---|---|---|---|---|
| TDDM (Borger) | 18.0487 | 9.94 | 0.4220 | 4.25% | 3.70% | 87.1% |
| mC10M-UV | 18.0177 | 9.97 | 0.4754 | 4.77% | 4.09% | 85.7% |
| mC10M-AC | 18.0217 | 9.92 | 0.4946 | 4.99% | 4.16% | 83.5% |
| mC10M-UV crude | 18.025 | 9.94 | 0.4923 | 4.95% | 4.76% | 96.0% |
| mC10M-AC crude | 18.0143 | 9.95 | 0.4937 | 4.96% | 4.76% | 95.9% |

In Table 5, the mass of each material used in the test is recorded in the first three columns. Percent mercaptan as percent of styrene is simply $(g_{mercaptan}/g_{styrene}) \times 100$. Percent partition in styrene is defined by (% mercaptan$_{by\ GC}$)/(% mercaptan$_{as\ \%\ styrene}) \times 100$.

None of the compositions produced via the reaction of mixed decenes with $H_2S$ in the presence of the HDS catalyst were tested in the emulsion polymerization or partitioning procedures. However, because the composition of the reaction product produced using the HDS catalyst is essentially a blend of the compositions produced using a UV-initiator and an acid catalyst, as shown by the gas chromatograph results in FIG. 8, it is expected that compositions derived from the crude reaction product from the HDS-catalyzed reaction would produce very similar results to those observed for the products of UV-initiated and acid-catalyzed reactions (i.e., the $C_{10}$ mercaptans produced via HDS catalysis would exhibit a similar value for the chain transfer constant and perform comparably as a chain transfer agent).

The results presented here show that mixed decyl mercaptans produced via both UV-initiated and acid catalyzed reactions function as chain transfer agents in emulsion polymerization at a level comparable to, if not better than the standard, TDDM. Additionally, the UV-initiated mixed decyl mercaptans exhibited a higher chain transfer constant compared to that of the reaction product formed from acid catalysis. Compositions comprising primarily only the $C_{10}$ mixed decyl mercaptans performed better than a composition comprising $C_{20}$ sulfides and other heavies, as the presence of sulfides/heavies resulted in a greater than 60% decrease in the chain transfer constant when approximately 20% sulfides were present. Without wishing to be bound by theory, results suggest that better chain transfer constants will be obtained with the use of purified mixed decyl mercaptans as chain transfer agents. Partitioning tests indicated that purified mixed decyl mercaptans have a similar preference for the organic phase as TDDM. Without wishing to be bound by theory, the shorter carbon chain length of the $C_{10}$ molecules should have little effect on CTA performance. The unpurified reaction product (consisting of $C_{10}$ mercaptans and $C_{20}$ sulfides), not surprisingly, partitions more to the organic phase than TDDM which should favor chain transfer; however, the presence of sulfides in the crude kettle-grade product seems to interfere with CTA performance.

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

Embodiment 1 is a chain transfer agent composition comprising at least one branched $C_{10}$ mercaptan selected from 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, or combinations thereof.

Embodiment 2 is the chain transfer agent composition of embodiment 1, wherein the at least one branched $C_{10}$ mercaptan is present in an amount of at least 30 wt. % based on a total weight of the chain transfer agent composition.

Embodiment 3 is the chain transfer agent composition of any of embodiments 1 to 2 further comprising one or more of a $C_{12}$ mercaptan, a $C_{14}$ mercaptan, a $C_{16}$ mercaptan, a $C_{18}$ mercaptan, or combinations thereof.

Embodiment 4 is the chain transfer agent composition of any of embodiments 3 to 4, wherein the at least one branched $C_{10}$ mercaptan, the $C_{12}$ mercaptan, the $C_{14}$ mercaptan, the $C_{16}$ mercaptan, and the $C_{18}$ mercaptan are present in an amount of at least 85 wt. % based on a total weight of the chain transfer agent composition.

Embodiment 5 is the chain transfer agent composition of any of embodiments 1 to 4, comprising less than about 10 wt. % $C_{16-36}$ sulfides based on a total weight of the chain transfer agent composition.

Embodiment 6 is the chain transfer agent composition of any of embodiments 1 to 5, wherein the chain transfer agent composition has an odor which is less unpleasant than an odor of mercaptan compounds which include n-dodecyl mercaptans, tert-dodecyl mercaptans, or combinations thereof present in an amount of equal to or greater than about 25 wt. % of the mercaptan compounds in an otherwise similar chain transfer agent composition.

Embodiment 7 is an emulsion polymerization reaction mixture comprising a chain transfer agent composition, optionally one or more monomer; optionally one or more surfactant; optionally one or more polymerization initiator; and optionally water. The chain transfer agent composition comprises at least one branched $C_{10}$ mercaptan selected from 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, or combinations thereof.

Embodiment 8 is the emulsion polymerization reaction mixture of embodiment 7, wherein the chain transfer agent composition is present in an amount of about 0.01 wt. % to about 5 wt. %. % based on a total weight of the emulsion polymerization mixture.

Embodiment 9 is the emulsion polymerization reaction mixture of any of embodiments 7 to 8, wherein the at least one branched $C_{10}$ mercaptan is present in an amount of at least 30 wt. % based on a total weight of the chain transfer agent composition.

Embodiment 10 is the emulsion polymerization reaction mixture of any of embodiments 7 to 9, wherein the chain transfer agent composition further comprises one or more of a $C_{12}$ mercaptan, a $C_{14}$ mercaptan, a $C_{16}$ mercaptan, a $C_{18}$ mercaptan, or combinations thereof.

Embodiment 11 is the emulsion polymerization reaction mixture of embodiment 10, wherein the at least one branched $C_{10}$ mercaptan, the $C_{12}$ mercaptan, the $C_{14}$ mercaptan, the $C_{16}$ mercaptan, and the $C_{18}$ mercaptan are present in an amount of at least 85 wt. % based on a total weight of the chain transfer agent composition.

Embodiment 12 is the emulsion polymerization reaction mixture of any of embodiments 7 to 11, wherein the chain transfer agent composition includes less than about 10 wt. % $C_{16-36}$ sulfides based on a total weight of the chain transfer agent composition.

Embodiment 13 is the emulsion polymerization reaction mixture of any of embodiments 7 to 12, being capable of free radical polymerization.

Embodiment 14 is a process for emulsion polymerization comprising introducing into an emulsion polymerization mixture a chain transfer agent composition comprising at least one branched $C_{10}$ mercaptan. The at least one branched $C_{10}$ mercaptan is selected from 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, or combinations thereof.

Embodiment 15 is the process of embodiment 14, wherein the chain transfer agent composition is present in an amount of about 0.01 wt. % to about 5 wt. %. % based on a total weight of the emulsion polymerization mixture.

Embodiment 16 is the process of any of embodiments 14 to 15, wherein the at least one branched $C_{10}$ mercaptan is present in an amount of at least 30 wt. % based on a total weight of the chain transfer agent composition.

Embodiment 17 is the process of any of embodiments 14 to 16, wherein the chain transfer agent composition further comprises one or more of a $C_{12}$ mercaptan, a $C_{14}$ mercaptan, a $C_{16}$ mercaptan, a $C_{18}$ mercaptan, or combinations thereof.

Embodiment 18 is the process of embodiment 17, wherein the at least one branched $C_{10}$ mercaptan, the $C_{12}$ mercaptan, the $C_{14}$ mercaptan, the $C_{16}$ mercaptan, and the $C_{18}$ mercaptan are present in an amount of at least 85 wt. % based on a total weight of the chain transfer agent composition.

Embodiment 19 is the process of any of embodiments 14 to 18, wherein the chain transfer agent composition includes less than about 10 wt. % $C_{16-36}$ sulfides based on a total weight of the chain transfer agent composition.

Embodiment 20 is the process of any of embodiments 14 to 19, wherein the emulsion polymerization mixture comprises one or more monomer, on or more surfactant, one or more polymerization initiator, and water.

Embodiment 21 is the process of any of embodiments 14 to 20, wherein the emulsion polymerization mixture comprises at least one component capable of free radical polymerization.

Embodiment 22 is the process of any of embodiments 14 to 21, further comprising forming the emulsion polymerization mixture comprising one or more monomer, one or more surfactant, optionally one or more polymerization initiator, water, or combinations thereof; and after the step of introducing, recovering a polymer form the emulsion polymerization mixture.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:
1. A process for emulsion polymerization comprising:
  contacting a chain transfer agent composition with one or more monomers, one or more surfactants, one or more polymerization initiators, and water to form an emulsion polymerization mixture; and
  recovering a polymer from the emulsion polymerization mixture,
wherein the chain transfer agent composition comprises mercaptans, wherein at least about 50 wt. % of the mercaptans are branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof

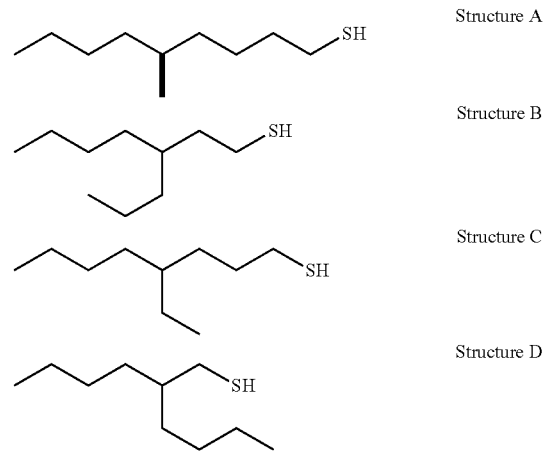

-continued

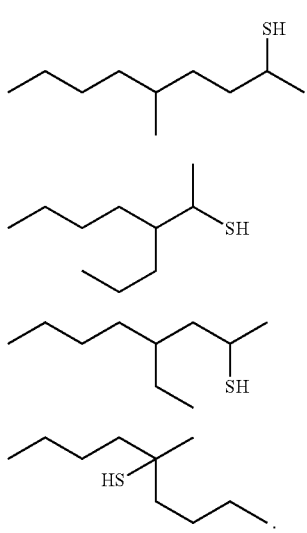

Structure E

Structure F

Structure G

Structure H

2. A process for emulsion polymerization comprising:
contacting a chain transfer agent composition with one or more monomers, one or more surfactants, one or more polymerization initiators, and water to form an emulsion polymerization mixture; and
recovering a polymer from the emulsion polymerization mixture, wherein the chain transfer agent composition comprises sulfides, wherein at least about 50 wt. % of the sulfides are branched $C_{20}$ sulfides represented by the structure $R^1$—S—$R^2$, wherein $R^1$ and $R^2$ are each independently a functional group derived from an olefine, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof,

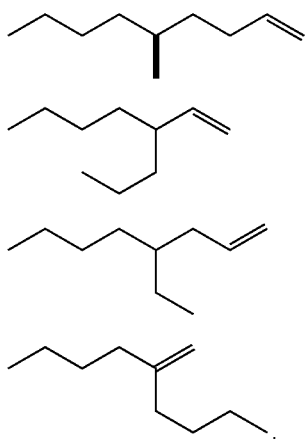

Structure I

Structure J

Structure K

Structure L

3. A process for emulsion polymerization comprising:
contacting a chain transfer agent composition with one or more monomers, one or more surfactants, one or more polymerization initiators, and water to form an emulsion polymerization mixture; and
recovering a polymer from the emulsion polymerization mixture,
wherein the chain transfer composition comprises:
(A) at least about 25 wt. % $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and
(B) at least about 5 wt. % $C_{20}$ sulfides represented by the structure $R^1$—S—$R^2$, wherein $R^1$ and $R^2$ are each independently a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

4. A process for emulsion polymerization comprising:
contacting a chain transfer agent composition with one or more monomers, one or more surfactants, one or more polymerization initiators, and water to form an emulsion polymerization mixture; and
recovering a polymer from the emulsion polymerization mixture,
wherein the chain transfer composition comprises:
(A) from at least about 50 wt. to at least about 90 wt. % mercaptans, wherein at least about 50 wt. % of the mercaptans are branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and
(B) from at least about 10 wt. % to at least about 30 wt. % sulfides, wherein at least 50 wt. % of the sulfides are branched $C_{20}$ sulfides represented by the structure $R^1$—S—$R^2$, wherein $R^1$ and $R^2$ are each independently a functional group derived from an olefin selected from the group consisting of 5-methyl-1-nonene (represented by Structure I), 3-propyl-1-heptene (represented by Structure J), 4-ethyl-1-octene (represented by Structure K), 2-butyl-1-hexene (represented by Structure L), and combinations thereof.

5. A process for emulsion polymerization comprising:
contacting a chain transfer agent composition with one or more monomers, One or more surfactants, one or more polymerization initiators, and water to form an emulsion polymerization mixture; and
recovering a polymer from the emulsion polymerization mixture,
wherein the chain transfer composition comprising:
(A) at least about 25 wt. % $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof;

(B) at least about 5 wt. % $C_{20}$ sulfides represented by the structure $R^1$—S—$R^2$, wherein $R^1$ and $R^2$ are each independently a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof; and one or more of the following components (C)-(I):

(C) less than about 5 wt. % $C_8$ mercaptans;

(D) less than about 15 wt. % $C_{12}$ mercaptans;

(E) less than about 15 wt. % $C_{14}$ mercaptans;

(F) less than about 5 wt. % $C_{16}$ mercaptans and/or $C_{18}$ mercaptans;

(G) less than about 1 wt. % $C_{16-36}$ sulfides represented by the structure $R^3$—S—$R^4$, wherein $R^3$ and $R^4$ are each independently a functional group derived from an olefin selected from the group consisting of $C_8$ monoolefins, $C_{10}$ monoolefins, $C_{12}$ monoolefins, $C_{14}$ monoolefins, $C_{16}$ monoolefins, and $C_{18}$ monoolefins, wherein $R^3$ and $R^4$ are not both branched $C_{10}$ monoolefins;

(H) less than about 10 wt. % unreacted $C_{8-18}$ monoolefins; and (I) less than about 10 wt. % non-olefine impurities selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate.

6. The process of claim 2, wherein the olefin comprises a) at least 76 mol % $C_{10}$ monoolefins, the $C_{10}$ monoolefins comprising i) at least 3 mol % 2-butyl-1-hexene (represented by Structure L), ii) at least 8 mol % 3-propyl-1-heptene (represented by Structure J), iii) at least 6 mol % 4-ethyl-1-octene (represented by Structure K), and iv) at least 20 mol % 5-methyl-1-nonene (represented by Structure I); and h) at least 1 mol % $C_{14}$ monoolefins.

7. The process of claim 6, wherein the $C_{10}$ monoolefins comprise from 1 mol % to 16 mol % 4-decene and/or 5-decene.

8. The process of claim 6, wherein the $C_{10}$ monoolefins comprise from 0.5 mol % to 9 mol % 1-decene.

9. The process of claim 2, wherein the olefin further comprises from 0.1 mol % to 5 mol % $C_{12}$ monoolefins, the $C_{12}$ monoolefins comprising from 54 mol % to 74 mol % 1-dodecene.

10. The process of claim 2, wherein the olefin further comprises from 0.1 mol % to 5 mol % $C_8$ monoolefins, the $C_8$ monoolefins comprising at least 95 mol % 1-octene.

11. The process of claim 1, wherein the olefin further comprises from 0.05 mol % to 2 mol % $C_{16}$ monoolefins and/or $C_{18}$ monoolefins.

* * * * *